US010251742B2

(12) United States Patent
Fujita et al.

(10) Patent No.: US 10,251,742 B2
(45) Date of Patent: Apr. 9, 2019

(54) ARTIFICIAL BLOOD VESSEL

(71) Applicant: Toray Industries, Inc., Tokyo (JP)

(72) Inventors: Masaki Fujita, Otsu (JP); Koji Kadowaki, Otsu (JP); Yuka Sakaguchi, Otsu (JP); Kazuhiro Tanahashi, Otsu (JP); Hiroshi Tsuchikura, Otsu (JP); Satoshi Yamada, Otsu (JP)

(73) Assignee: Toray Industries, Inc. (JP)

( * ) Notice: Subject to any disclaimer, the term of this patent is extended or adjusted under 35 U.S.C. 154(b) by 94 days.

(21) Appl. No.: 15/117,941

(22) PCT Filed: Feb. 12, 2015

(86) PCT No.: PCT/JP2015/053749
§ 371 (c)(1),
(2) Date: Aug. 10, 2016

(87) PCT Pub. No.: WO2015/122429
PCT Pub. Date: Aug. 20, 2015

(65) Prior Publication Data
US 2016/0354194 A1    Dec. 8, 2016

(30) Foreign Application Priority Data
Feb. 12, 2014    (JP) .................... 2014-024625

(51) Int. Cl.
| *A61F 2/06* | (2013.01) |
| *A61F 2/89* | (2013.01) |
| *D03D 3/02* | (2006.01) |
| *D03D 15/00* | (2006.01) |
| *A61L 27/50* | (2006.01) |
| *A61L 33/00* | (2006.01) |
| *A61L 27/18* | (2006.01) |
| *A61L 33/06* | (2006.01) |

(52) U.S. Cl.
CPC .............. *A61F 2/06* (2013.01); *A61L 27/18* (2013.01); *A61L 27/507* (2013.01); *A61L 33/0076* (2013.01); *A61L 33/068* (2013.01); *D03D 3/02* (2013.01); *D03D 15/0061* (2013.01); *A61F 2210/0076* (2013.01); *A61F 2230/0069* (2013.01); *A61L 2300/42* (2013.01); *D10B 2509/06* (2013.01)

(58) Field of Classification Search
CPC .............. A61F 2/06; A61F 2/062; A61F 2/89
See application file for complete search history.

(56) References Cited

U.S. PATENT DOCUMENTS

| 3,350,488 A | 10/1967 | Breen |
| 3,531,368 A | 9/1970 | Okamoto et al. |
| 4,695,280 A * | 9/1987 | Watanabe ................ A61F 2/06 |
| | | 623/1.39 |
| 4,743,250 A | 5/1988 | Kitagawa et al. |
| 5,254,249 A * | 10/1993 | Terada ................ A61L 33/0029 |
| | | 210/321.62 |
| 5,451,428 A * | 9/1995 | Rupp ................ A61L 33/0029 |
| | | 427/2.12 |
| 5,986,168 A | 11/1999 | Noishiki |
| 2004/0213818 A1 | 10/2004 | Kashiwabara et al. |
| 2005/0064038 A1 | 3/2005 | Dinh et al. |
| 2005/0070479 A1 | 3/2005 | Steinmetzer et al. |
| 2010/0176048 A1 | 7/2010 | Sakaguchi et al. |
| 2011/0065085 A1 | 3/2011 | Biran et al. |
| 2011/0084019 A1* | 4/2011 | Shiratori ................ A61L 27/34 |
| | | 210/506 |
| 2012/0116492 A1 | 5/2012 | Seibold et al. |
| 2013/0041452 A1* | 2/2013 | Fujita .................... D04B 21/16 |
| | | 623/1.13 |
| 2014/0113091 A1 | 4/2014 | Sakaguchi et al. |
| 2015/0081004 A1* | 3/2015 | Takahashi ................ D01F 6/62 |
| | | 623/1.11 |

FOREIGN PATENT DOCUMENTS

| JP | 60-41947 B2 | 9/1985 |
| JP | 60-47287 B2 | 10/1985 |
| JP | 61/4546 B2 | 2/1986 |
| JP | 61/58190 B2 | 12/1986 |
| JP | 63/52898 B2 | 10/1988 |
| JP | 5-28143 B2 | 4/1993 |
| JP | 5-48132 B2 | 7/1993 |
| JP | 5-88611 B2 | 12/1993 |
| JP | 7-265338 A | 10/1995 |

(Continued)

OTHER PUBLICATIONS

P. C. Begovac, et al , "Improvements in GORE-TEX® Vascular Graft Performance by Carmeda® BioActive Surface Heparin Immobilization", *Eur J Vasc Endovasc Surg*, 25, 2003, pp. 432-437.

*Primary Examiner* — Christopher D. Prone
*Assistant Examiner* — Christine L Nelson
(74) *Attorney, Agent, or Firm* — DLA Piper LLP (US)

(57) ABSTRACT

An artificial blood vessel is composed of a cylindrical multiple-woven fabric structure allowing only a small amount of blood leakage and can achieve both antithrombogenicity and cellular affinity. The artificial blood vessel includes a cylindrical fabric structure in which a cylindrical fabric whose inside contacts blood is arranged, wherein the cylindrical fabric is a fabric prepared by interlacing a plurality of warp yarns and a plurality of weft yarns with each other into a cylindrical shape; the warp yarns and the weft yarns constituting the cylindrical fabric include a multifilament yarn having a single yarn fineness of not more than 0.50 dtex, and are bound to an antithrombogenic material; the antithrombogenic material forms an antithrombogenic material layer having a thickness of 1 to 600 nm inside the cylindrical fabric; and the water permeability under conditions where a pressure of 16 kPa is applied to the inner surface is less than 300 mL/cm²/min.

7 Claims, No Drawings

(56) References Cited

FOREIGN PATENT DOCUMENTS

| | | |
|---|---|---|
| JP | 8-24686 B2 | 3/1996 |
| JP | 10-151192 A | 6/1998 |
| JP | 3497612 B2 | 2/2004 |
| JP | 3799626 B2 | 7/2006 |
| JP | 2008-511339 | 4/2008 |
| JP | 4152075 B2 | 9/2008 |
| JP | 4273965 B2 | 6/2009 |
| JP | 2009-545333 A | 12/2009 |
| JP | 4461217 B2 | 5/2010 |
| JP | 2013-505070 A | 2/2013 |
| WO | 00/13718 A1 | 3/2000 |
| WO | 2007-133699 A2 | 11/2007 |
| WO | 2008/032758 A1 | 3/2008 |
| WO | 2009/119761 A1 | 10/2009 |
| WO | 2011/136243 A1 | 11/2011 |
| WO | 2012/176861 A1 | 12/2012 |
| WO | 2013/137263 A1 | 9/2013 |

\* cited by examiner

ARTIFICIAL BLOOD VESSEL

TECHNICAL FIELD

This disclosure relates to a fabric artificial blood vessel that allows only a small amount of blood leakage and can achieve both antithrombogenicity and cellular affinity.

BACKGROUND

An artificial blood vessel is a medical device used as an alternative to a living blood vessel suffering from a disease such as arteriosclerosis, or for formation of a bypass or a shunt. Conventional artificial blood vessels can be roughly divided into 1) artificial blood vessels made of a fabric; 2) artificial blood vessels made of polytetrafluoroethylene; 3) artificial blood vessels made of a biomaterial; and 4) artificial blood vessels made of a synthetic macromolecular material. Among these artificial blood vessels, fabric artificial blood vessels made of a woven fabric, knit, or non-woven fabric of fibers have high flexibility, but have a drawback in that blood leakage from gaps between fibers is likely to occur due to blood pressure under actual use conditions. Among fabric artificial blood vessels, knitted artificial blood vessels can be produced by a simple production process, and have flexibility. However, they have lower capacities to maintain their shapes and are likely to have porous structures so that blood leakage is likely to occur through gaps between fibers. Artificial blood vessels made of a non-woven fabric have uneven structures, and have lower capacities to maintain their shapes, which is not preferred.

On the other hand, in fabric artificial blood vessels composed of a woven fabric, the gaps between the fibers can be reduced, and the amount of blood leakage can therefore be reduced unlike artificial blood vessels made of a knit. Therefore, fabric artificial blood vessels composed of a woven fabric are highly demanded in surgery of blood vessels such as aortas. As a method of reducing the amount of blood leakage, a method by reducing the size of each gap between fibers is commonly used. However, in that method, the resulting artificial blood vessel is hard because of an increase in the fiber density. Use of such a hard artificial blood vessel often makes the surgery difficult since both ends of the diseased living blood vessel to be replaced, that is, the living blood vessels to be anastomosed with the artificial blood vessel, are also affected by arteriosclerosis or the like.

In view of this, when a fabric artificial blood vessel is used in blood vessel surgery, a method in which blood leakage is prevented not only by reducing the size of each gap between fibers, but also by giving a bioabsorbable gel such as collagen or gelatin to the gaps between the fibers to fill the gaps, has been reported (JP 3799626 B).

Methods in which the so-called preclotting is carried out have also been reported (JP 5-48132 B and JP 5-88611 B). In the operation of preclotting, a fabric artificial blood vessel is brought into contact with autologous blood immediately before transplantation, to allow formation of thrombi, and the gaps between the fibers are filled with the resulting thrombi to prevent blood leakage.

When an artificial blood vessel is transplanted, the living body recognizes it as a foreign substance, and blood coagulation reaction proceeds on the surface of the artificial blood vessel contacting blood, that is, on the inner surface, leading to formation of thrombi. Therefore, artificial blood vessels require antithrombogenicity.

Conventionally, as a method of increasing the antithrombogenicity of a medical material, a method in which heparin or a heparin derivative is given to a surface of the material has been employed. However, heparin and heparin derivatives cannot be directly given to fabric medical materials made of polyester fibers and the like, and medical materials made of stretched porous polytetrafluoroethylene (hereinafter referred to as "ePTFE"), which constitute artificial blood vessels. In view of this, methods in which a surface of a medical material is modified, and heparin or a heparin derivative is given to the surface of the material by covalent bonding (Japanese Translated PCT Patent Application Laid-open No. 2009-545333, JP 4152075 B and JP 3497612 B), or heparin or a heparin derivative is given to the surface of the material by ionic bonding (JP 60-41947 B, JP 60-47287 B, JP 4273965 B and JP 10-151192 A), have been reported.

As methods of giving antithrombogenicity to a fabric artificial blood vessel, methods in which a bioabsorbable gel used for preventing blood leakage, for example, collagen or gelatin, is impregnated with heparin or a heparin derivative, and the resulting gel is given to a surface of a material (JP 3799626 B and JP 8-24686 B), and a method in which a segmented polyurethane dissolved in an organic solvent is impregnated with heparin or a heparin derivative, and the resulting product is given to a surface of a material (JP 7-265338 A), have been reported.

As methods of increasing the antithrombogenicity of a medical material using a compound having antithrombogenicity other than heparin or heparin derivatives, methods in which a compound(s) that inhibit(s) a plurality of blood coagulation factors involved in the blood coagulation reaction (for example, platelets, which are involved in the stage of primary hemostasis), thrombin, which is involved in the stage of thrombus formation, and/or the like is/are given to a surface of the medical material (JP 4461217 B, WO 08/032758 and WO 12/176861) have been reported.

Living blood vessels have an intima on their inner surfaces, and can inhibit thrombus formation by having vascular endothelial cells. On the other hand, in conventional artificial blood vessels, the cellular affinity is low, and settlement of vascular endothelial cells is less likely to occur. Moreover, settlement of vascular endothelial cells and formation of the intima take a long time. Therefore, not only antithrombogenicity immediately after the transplantation, but also a function to generate cellular affinity with time, have been required.

Examples of reported methods of giving cellular affinity to a fabric artificial blood vessel include methods in which an artificial blood vessel is made such that it has a fiber structure which promotes growth and infiltration of cells such as a method in which the fiber diameter is optimized, and a method in which fluffy, fuzzy, and/or looped fibers are given (JP 61-4546 B, JP 61-58190 B, JP 63-52898 B and JP 5-28143 B).

However, when the method disclosed in JP 3799626 B is used for a fabric artificial blood vessel, the fiber diameter and microstructures such as gaps between fibers for promotion of the cell growth disappear due to the gel such as collagen or gelatin containing heparin or a heparin derivative given to the fiber surface, leading to a decrease in the cellular affinity. Moreover, adhesion of platelets to the bioabsorbable gel such as gelatin rather promotes thrombus formation, which is problematic.

On the other hand, JP 5-48132 B and JP 5-88611 B disclose methods of preparing an artificial blood vessel having a high-porosity structure, that is, a high-water permeability woven structure, to allow quick settlement of vascular endothelial cells on the inner surface of the artificial blood vessel, thereby promoting formation of the intima, or to reduce foreign substances, thereby increasing the biocompatibility, respectively. However, preclotting is indispensable in these methods, and the fiber diameter and microstructures such as gaps between fibers disappear due to thrombi formed by this operation, leading to a decrease in the cellular affinity. In blood vessel surgery, an anticoagulant (for example, heparin or argatroban) is commonly used for prevention of blood coagulation during the surgery, and the blood vessel is therefore in a state where a thrombus is less likely to be formed. Thus, in some cases, the gaps between the fibers cannot be sufficiently filled by the preclotting. Furthermore, in some cases, thrombi formed by the preclotting are melted due to the action of the fibrinolytic system in blood after the surgery, leading to blood leakage.

Japanese Translated PCT Patent Application Laid-open No. 2009-545333, JP 4152075 B, JP 3497612 B, JP 60-41947 B, JP 60-47287 B, JP 4273965 B and JP 10-151192 A describe methods in which heparin or a heparin derivative is given to a surface of a medical material by covalent or ionic bonding of the heparin or the heparin derivative to a surface modifier. However, in terms of use of a fabric artificial blood vessel having a fiber diameter and/or a microstructure such as gaps between fibers for promotion of the cell growth, those publications do not describe an appropriate thickness of the antithrombogenic material layer composed of the surface modifier and the heparin or the heparin derivative.

JP 8-24686 B and JP 7-265338 A describe methods in which a bioabsorbable gel containing heparin or a heparin derivative, or an antithrombogenic material dissolved in an organic solvent, is physically given to a surface of a medical material. Since, in those methods, the antithrombogenic material layer is thick, the fiber diameter and microstructures such as gaps between fibers for promotion of the cell growth disappear.

Similarly, JP 4461217 B, WO 08/032758 and WO 12/176861 describe methods in which two compounds having both anti-platelet adhesion capacity and antithrombin activation capacity, or a compound prepared by giving both anti-platelet adhesion capacity and antithrombin activation capacity to a single molecule, is/are immobilized on a surface of a medical material. However, in terms of use for a fabric artificial blood vessel having a fiber diameter and/or a microstructure such as gaps between fibers for promotion of the cell growth, those publications do not describe appropriate thickness of the antithrombogenic material layer composed of such a compound(s).

JP 61-4546 B, JP 61-58190 B, JP 63-52898 B and JP 5-28143 B disclose artificial blood vessels having cellular affinity prepared using a fiber of not more than 0.5 denier, that is, not more than 0.56 dtex, for at least a part of the inner surface. However, since antithrombogenicity, which is required immediately after the transplantation, is not given to those artificial blood vessels, they cannot suppress thrombus formation. Although a method of increasing the cellular affinity by giving fluffy, fuzzy, and/or looped fibers has been disclosed, such a method has a problem in that an additional step of forming the fluffy, fuzzy, and/or looped fibers is required, and that this additional step produces waste fibers whose elution into blood may occur. Moreover, that method has a problem in that, since disturbance of the fiber directions of the warp yarns and the weft yarns increases, settlement of vascular endothelial cells is less likely to occur, and the cellular affinity therefore decreases.

That is, at present, there is no artificial blood vessel composed of a cylindrical fabric structure that allows only a small amount of blood leakage and can achieve both the antithrombogenicity and the cellular affinity. In particular, in a small-diameter artificial blood vessel having an inner diameter of less than 6 mm, thrombi are likely to be formed because of low blood flow, and even a small thrombus may have a size comparable to the inner diameter of the blood vessel. Thus, inhibition of the blood flow is likely to occur. Therefore, small-diameter artificial blood vessels show poor long-term performances, and none of them is clinically useful at present.

It could therefore be helpful to provide a fabric artificial blood vessel that allows only a small amount of blood leakage and can achieve both the antithrombogenicity and the cellular affinity.

SUMMARY

We thus provide:

(1) An artificial blood vessel comprising a cylindrical fabric structure in which a cylindrical fabric whose inside contacts blood is arranged, wherein the cylindrical fabric whose inside contacts blood is a fabric prepared by interlacing a plurality of warp yarns and a plurality of weft yarns with each other into a cylindrical shape;

the warp yarns and the weft yarns constituting the cylindrical fabric whose inside contacts blood comprise a multifilament yarn having a single yarn fineness of not more than 0.50 dtex, and are bound to an antithrombogenic material;

the antithrombogenic material forms an antithrombogenic material layer having a thickness of 1 to 600 nm inside the cylindrical fabric whose inside contacts blood; and the water permeability under conditions where a pressure of 16 kPa is applied to the inner surface is less than 300 mL/cm$^2$/min.

(2) The artificial blood vessel according to (1), wherein the cylindrical fabric structure is a multi-cylindrical fabric structure in which an outer-layer cylindrical fabric is arranged outside the cylindrical fabric whose inside contacts blood, and the outer-layer cylindrical fabric is a fabric prepared by interlacing a plurality of warp yarns and weft yarns with each other into a cylindrical shape.

(3) The artificial blood vessel according to (2), wherein the outer-layer cylindrical fabric comprises, as a warp yarn, a multifilament yarn having a single yarn fineness of not less than 1.0 dtex.

(4) The artificial blood vessel according to (3), wherein the percentage of exposure of the multifilament yarn having a single yarn fineness of not less than 1.0 dtex on the inner surface is not more than 20%.

(5) The artificial blood vessel according to any one of (1) to (4), wherein the cover factor for the warp yarns and the weft yarns constituting the cylindrical fabric whose inside contacts blood is 1800 to 4000.

(6) The artificial blood vessel according to any one of (2) to (5), wherein the outer-layer cylindrical fabric comprises, as a weft yarn, a monofilament yarn having a single yarn fineness of not less than 15.0 dtex.

(7) The artificial blood vessel according to any one of (1) to (6), wherein the antithrombogenic material comprises an anionic compound containing a sulfur atom and having anticoagulant activity.

(8) The artificial blood vessel according to (7), wherein the ratio of the abundance of sulfur atoms to the abundance of total atoms on the inner surface as measured by X-ray photoelectron spectroscopy (XPS) is 3.0 to 6.0 atomic percent.

(9) The artificial blood vessel according to any one of (1) to (8), wherein the antithrombogenic material comprises a cationic polymer containing, as a constituent monomer, a compound selected from the group consisting of alkyleneimines, vinylamines, allylamines, lysine, protamine, and diallyldimethylammonium chloride, and the cationic polymer is covalently bound to the warp yarns and the weft yarns constituting the cylindrical fabric whose inside contacts blood.

(10) The artificial blood vessel according to any one of (1) to (6), wherein the antithrombogenic material is a compound containing the following three kinds of skeletal structures: a skeletal structure composed of a hydrophilic polymer containing, as a constituent monomer, a compound selected from the group consisting of ethylene glycol, propylene glycol, vinylpyrrolidone, vinyl alcohol, vinylcaprolactam, vinyl acetate, styrene, methyl methacrylate, hydroxyethyl methacrylate, and siloxane; a skeletal structure composed of 4-(aminomethyl)benzenecarboxyimidamide or benzene amidine; and a skeletal structure composed of methoxybenzenesulfonic acid amide; wherein the compound containing the three kinds of skeletal structures is covalently bound to the warp yarns and the weft yarns constituting the cylindrical fabric whose inside contacts blood.

(11) The artificial blood vessel according to (10), wherein the compound containing the three kinds of skeletal structures is a compound represented by any one of General Formulae (I) to (IV):

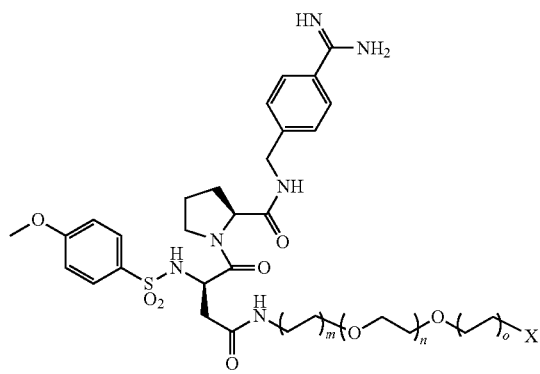

(I)

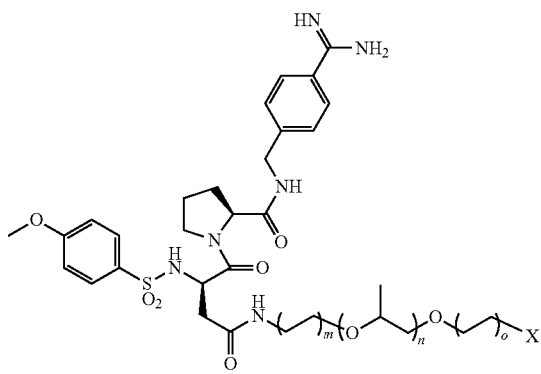

(II)

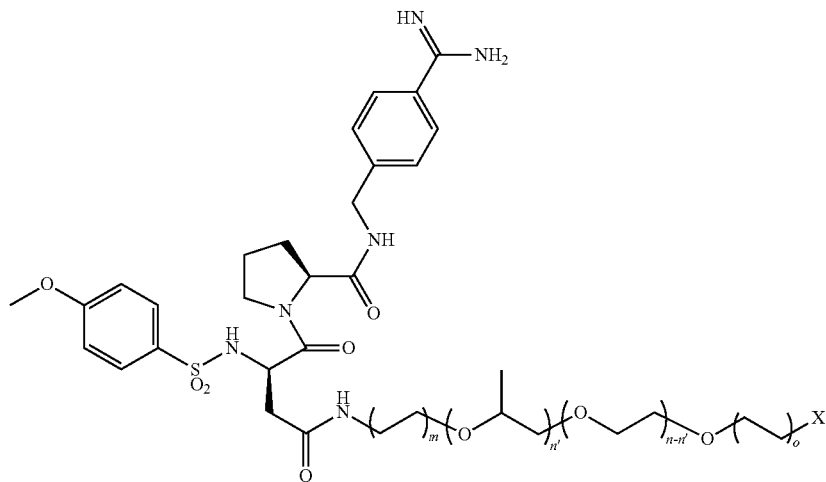

(III)

-continued

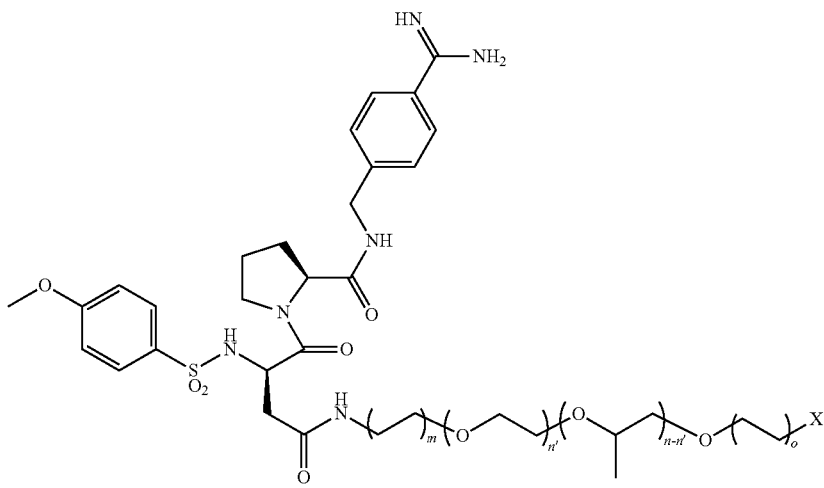

(IV)

wherein m and o each represent an integer of 0 to 4; n represents an integer of 3 to 1000, and n' represents an integer of 3 to 1000, with the proviso that n>n'; and X represents a functional group selected from the group consisting of hydroxyl, thiol, amino, carboxyl, aldehyde, isocyanate, and thioisocyanate.

(12) The artificial blood vessel according to any one of (1) to (11), wherein the antithrombogenic material comprises: an anionic polymer comprising, as a constituent monomer, a compound selected from the group consisting of acrylic acid, methacrylic acid, α-glutamic acid, γ-glutamic acid, and aspartic acid; or an anionic compound selected from the group consisting of oxalic acid, malonic acid, succinic acid, fumaric acid, glutaric acid, adipic acid, pimelic acid, suberic acid, azelaic acid, sebacic acid, malic acid, tartaric acid, and citric acid.

(13) The artificial blood vessel according to any one of (1) to (12), wherein the multifilament yarn is composed of a polyester.

We also provide the artificial blood vessels according to (14) to (25).

(14) An artificial blood vessel comprising a multi-cylindrical fabric structure in which an inner-layer cylindrical fabric is arranged inside an outer-layer cylindrical fabric, wherein each of the outer-layer cylindrical fabric and the inner-layer cylindrical fabric is a fabric prepared by interlacing a plurality of warp yarns and a plurality of weft yarns with each other into a cylindrical shape;

the warp yarns and the weft yarns constituting the inner-layer cylindrical fabric comprise a multifilament yarn having a single yarn fineness of not more than 0.30 dtex, and are bound to an antithrombogenic material;

the antithrombogenic material forms an antithrombogenic material layer having a thickness of 1 to 600 nm inside the inner-layer cylindrical fabric; and the water permeability under conditions where a pressure of 16 kPa is applied to the inner surface is less than 300 mL/cm²/min.

(15) The artificial blood vessel according to (14), wherein the outer-layer cylindrical fabric comprises, as a warp yarn, a multifilament yarn having a single yarn fineness of not less than 1.0 dtex.

(16) The artificial blood vessel according to (15), wherein the percentage of exposure of the multifilament yarn having a single yarn fineness of not less than 1.0 dtex on the inner surface is not more than 20%.

(17) The artificial blood vessel according to any one of (14) to (16), wherein the outer-layer cylindrical fabric comprises, as a weft yarn, a monofilament yarn having a single yarn fineness of not less than 15.0 dtex.

(18) The artificial blood vessel according to any one of (14) to (17), wherein the antithrombogenic material comprises an anionic compound having anticoagulant activity and containing a sulfur atom.

(19) The artificial blood vessel according to (18), wherein the ratio of the abundance of sulfur atoms to the abundance of total atoms on the inner surface as measured by X-ray photoelectron spectroscopy (XPS) is 3.0 to 6.0 atomic percent.

(20) The artificial blood vessel according to any one of (1) to (19), wherein the antithrombogenic material comprises a cationic polymer containing, as a constituent monomer, a compound selected from the group consisting of alkyleneimines, vinylamines, allylamines, lysine, protamine, and diallyldimethylammonium chloride, and the cationic polymer is covalently bound to the warp yarns and the weft yarns constituting the inner-layer cylindrical fabric.

(21) The artificial blood vessel according to (20), wherein the ratio of the abundance of nitrogen atoms to the abundance of total atoms on the inner surface as measured by X-ray photoelectron spectroscopy (XPS) is 7.0 to 12.0 atomic percent.

(22) The artificial blood vessel according to any one of (14) to (17), wherein the antithrombogenic material is a compound containing the following three kinds of skeletal structures: a skeletal structure composed of a hydrophilic polymer containing, as a constituent monomer, a compound selected from the group consisting of ethylene glycol, propylene glycol, vinylpyrrolidone, vinyl alcohol, vinylcaprolactam, vinyl acetate, styrene, methyl methacrylate, hydroxyethyl methacrylate, and siloxane; a skeletal structure composed of 4-(aminomethyl)benzenecarboxyimidamide or benzene amidine; and a skeletal structure composed of methoxybenzenesulfonic acid amide; wherein the compound containing the three kinds of skeletal structures is covalently bound to the warp yarns and the weft yarns constituting the inner-layer cylindrical fabric.

(23) The artificial blood vessel according to (22), wherein the compound containing the three kinds of skeletal structures is a compound represented by any one of General Formulae (I) to (IV):

(24) The artificial blood vessel according to any one of (14) to (23), wherein the antithrombogenic material comprises: an anionic polymer comprising, as a constituent monomer, a compound selected from the group consisting of

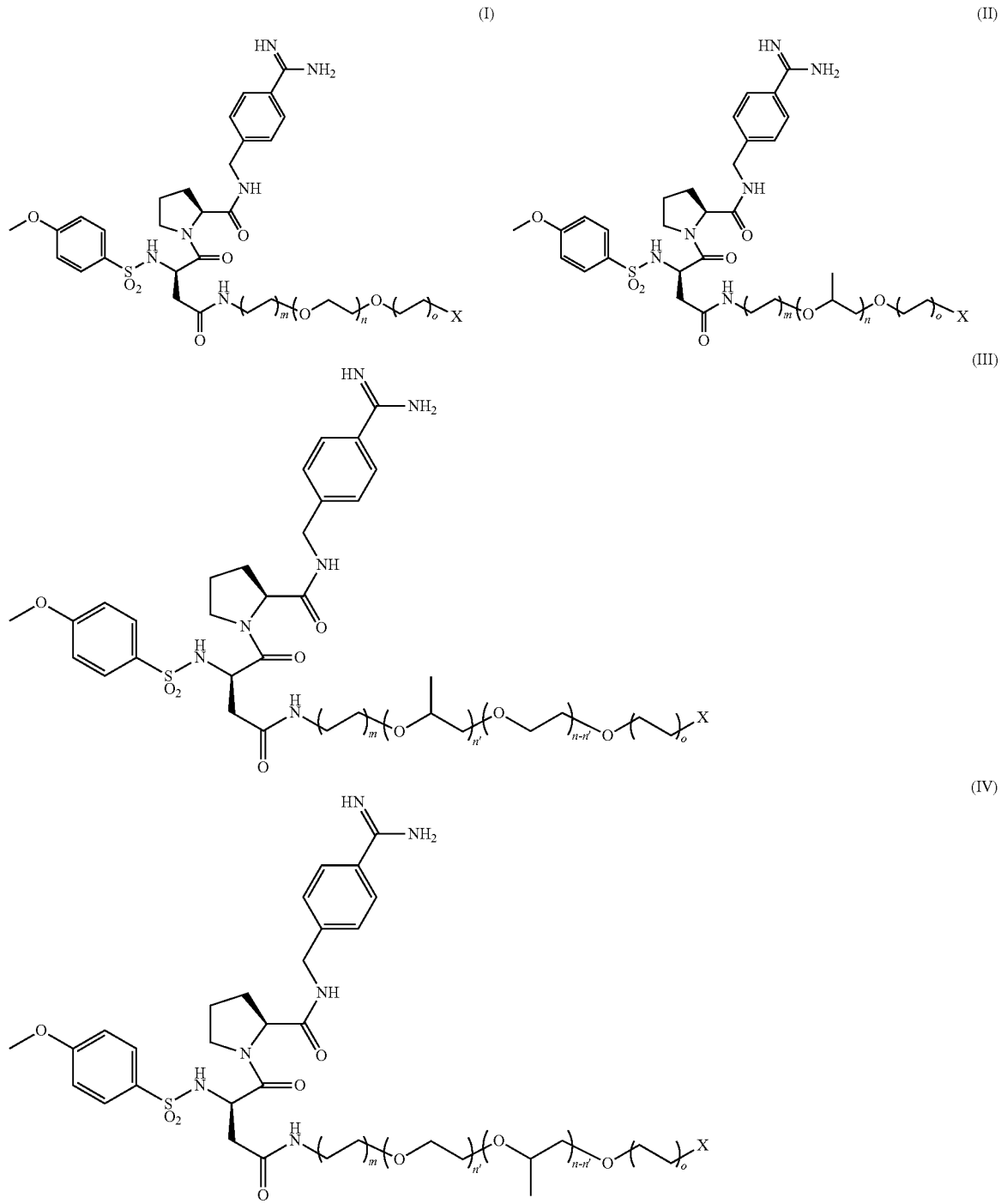

wherein m and o each represent an integer of 0 to 4; n represents an integer of 3 to 1000, and n' represents an integer of 3 to 1000, with the proviso that n>n'; and X represents a functional group selected from the group consisting of hydroxyl, thiol, amino, carboxyl, aldehyde, isocyanate, and thioisocyanate.

acrylic acid, methacrylic acid, α-glutamic acid, γ-glutamic acid, and aspartic acid; or an anionic compound selected from the group consisting of oxalic acid, malonic acid, succinic acid, fumaric acid, glutaric acid, adipic acid, pimelic acid, suberic acid, azelaic acid, sebacic acid, malic acid, tartaric acid, and citric acid.

(25) The artificial blood vessel according to any one of (14) to (24), wherein the multifilament yarn is composed of a polyester.

The fabric artificial blood vessel allows only a small amount of blood leakage, and can achieve both the antithrombogenicity and the cellular affinity.

DETAILED DESCRIPTION

The artificial blood vessel is characterized in that, in a cylindrical fabric structure in which a cylindrical fabric whose inside contacts blood is arranged, the cylindrical fabric whose inside contacts blood is a fabric prepared by interlacing a plurality of warp yarns and a plurality of weft yarns with each other into a cylindrical shape;

the warp yarns and the weft yarns constituting the cylindrical fabric whose inside contacts blood comprise a multifilament yarn having a single yarn fineness of not more than 0.50 dtex, and are bound to an antithrombogenic material;

the antithrombogenic material forms an antithrombogenic material layer having a thickness of 1 to 600 nm inside the cylindrical fabric whose inside contacts blood; and the water permeability under conditions where a pressure of 16 kPa is applied to the inner surface is less than 300 mL/cm$^2$/min.

The following terms are defined as described below unless otherwise specified.

The cylindrical fabric means a fabric prepared by interlacing a plurality of warp yarns and a plurality of weft yarns with each other into a cylindrical shape. In the artificial blood vessel, a structure in which a cylindrical fabric whose inside contacts blood is arranged is defined as a cylindrical fabric structure. In the artificial blood vessel, the cylindrical fabric whose inside contacts blood is defined as an inner-layer cylindrical fabric; the cylindrical fabric forming the outer layer of the artificial blood vessel is defined as an outer-layer cylindrical fabric; and the structure in which the outer-layer cylindrical fabric and the inner-layer cylindrical fabric are laminated with each other is defined as a multi-cylindrical fabric structure. The multi-cylindrical fabric structure constituting the artificial blood vessel may contain a cylindrical fabric layer other than the inner-layer cylindrical fabric and the outer-layer cylindrical fabric. However, when the number of cylindrical fabric layers is too large, the artificial blood vessel is thick, and therefore the difference between the thickness of the artificial blood vessel and the thickness of the living blood vessel is large. This causes difficulty in anastomosis in the transplantation surgery. In view of this, the number of cylindrical fabric layers is preferably 2 to 4, more preferably 2 to 3. Double-woven artificial blood vessels, whose number of cylindrical fabric layers is 2, can be integrally woven by a well-known method such as inner-layer warp yarn fastening, inner-layer weft yarn fastening, or multi-weft yarn fastening. When double weaving is carried out, the process of laminating the two fabrics with each other by a method such as lamination or sewing is not necessary, and, since the two layers are integrated with each other through warp yarns or weft yarns, the artificial blood vessel obtained can have high flexibility and high mechanical strength.

The single yarn fineness means a value calculated according to the JIS L 1013 (2010) 8.3.1 A method, in which the fineness based on corrected weight is measured at a predetermined load of 0.045 cN/dtex to determine the total fineness, and the total fineness is then divided by the number of monofilaments.

When the single yarn fineness of the warp yarns and the weft yarns constituting the cylindrical fabric whose inside contacts blood is too large, when the yarns are tightly woven to reduce the amount of blood leakage, the resulting artificial blood vessel is hard, and moreover, settlement of vascular endothelial cells is less likely to occur so that the cellular affinity is low. On the other hand, when the single yarn fineness is too small, the mechanical strength of the artificial blood vessel is less likely to be maintained, and settlement of vascular endothelial cells is less likely to occur. That is, we discovered that, on the inner surface of the artificial blood vessel which contacts blood, the warp yarns and the weft yarns constituting the cylindrical fabric whose inside contacts blood preferably comprise a multifilament yarn having a single yarn fineness of 0.05 to 0.50 dtex, more preferably comprise a multifilament yarn having a single yarn fineness of 0.05 to 0.30 dtex, still more preferably comprise a multifilament yarn having a single yarn fineness of 0.06 to 0.28 dtex, still more preferably comprise a multifilament yarn having a single yarn fineness of 0.08 to 0.25 dtex. The inner surface means the surface inside the artificial blood vessel including the inside of the cylindrical fabric whose inside contacts blood, and the antithrombogenic material layer formed by binding of the antithrombogenic material to the inside of the cylindrical fabric whose inside contacts blood.

As the multifilament yarn having a single yarn fineness of not more than 0.50 dtex, the so-called direct-spun type may be used as it is. Alternatively, for example, a split-yarn type such as a sea-island composite fiber may be used as it is. In a split-yarn type, when fibers that can be made into ultrafine fibers by chemical or physical means are used, ultrafine fibers can be formed after formation of the artificial blood vessel. Examples of the method of forming the fibers into the ultrafine fibers by chemical or physical means include the methods described in U.S. Pat. No. 3,531,368 B and U.S. Pat. No. 3,350,488 B, wherein means such as removal or detachment of a component from multicomponent fibers is used to allow fibrillation of the fibers, or to make the fibers into ultrafine fibers. By this, even when a multifilament yarn having a single yarn fineness of more than 0.50 dtex is used, the fibers can be made into ultrafine fibers having a single yarn fineness of not more than 0.50 dtex after the formation of the artificial blood vessel. Therefore, troubles in the processing, for example, yarn breakage and fluffing associated with various yarn processing means during the weaving or before the weaving, can be minimized.

The bond means a chemical bond such as a covalent bond, hydrogen bond, ionic bond, or coordinate bond. The covalent bond means a chemical bond formed by sharing of an electron(s) between atoms. Examples of the type of the covalent bond include, but are not limited to, an amine bond, azide bond, amide bond, and imine bond. Among these, from the viewpoint of ease of formation of the covalent bond, stability after bonding, and the like, an amide bond is more preferred. The presence of covalent bonds can be continued by observing the fact that elution does not occur by washing of the artificial blood vessel with a solvent which dissolves the antithrombogenic material.

When the water permeability is too high, the sizes and the amount of the gaps between the fibers are large so that application of a gel such as collagen or gelatin, preclotting immediately before the transplantation, and/or the like may be necessary, which is not preferred. That is, we discovered that the water permeability under conditions where a pressure of 16 kPa is applied to the inner surface is preferably less than 300 mL/cm²/min, more preferably less than 200 mL/cm²/min., still more preferably less than 150 mL/cm²/min.

On the other hand, in a cylindrical fabric such as the one herein, low water permeability cannot be achieved only by controlling the gaps between the fibers, and its achievement requires an operation of application of a bioabsorbable gel such as collagen or gelatin, as in the known fabrics. In such a case, the fiber diameter and microstructures such as gaps between fibers for promotion of the cell growth disappear, leading to a decrease in the cellular affinity. Moreover, adhesion of platelets to the bioabsorbable gel such as gelatin rather promotes thrombus formation, which is problematic. That is, we discovered that the water permeability under conditions where a pressure of 16 kPa is applied to the inner surface is preferably more than 0.1 mL/cm²/min, more preferably more than 0.5 mL/cm²/min, still more preferably more than 1 mL/cm²/min.

The water permeability under conditions where a pressure of 16 kPa is applied to the inner surface means a value determined according to the guidance in ISO 7198 by applying a pressure (hydrostatic pressure) of 16 kPa to the inner surface of the artificial blood vessel, including the inside of the cylindrical fabric whose inside contacts blood, and the antithrombogenic material layer, and dividing the amount of water (mL) flown out into the outer layer of the artificial blood vessel by the unit area (cm²) and the unit time (min.). The thus determined water permeability can be used as an index representing the sizes and the amount of the gaps between the fibers of the artificial blood vessel. The water permeability can be adjusted by changing, for example, the component ratios of the warp yarns and the weft yarns constituting the cylindrical fabric whose inside contacts blood; the single yarn diameter; the packing density; and/or the thickness and the hydrophilicity of the antithrombogenic material layer.

When the ratio of the multifilament yarns having a single yarn fineness of not more than 0.50 dtex in the warp yarns and the weft yarns constituting the cylindrical fabric whose inside contacts blood is too low on the inner surface of the artificial blood vessel which contacts blood, the sizes and the amount of the gaps between the fibers are large so that the amount of blood leakage is large. Moreover, settlement of vascular endothelial cells is less likely to occur, and the cellular affinity is likely to be low. In view of this, we discovered that the ratio of the multifilament yarns having a single yarn fineness of not more than 0.50 dtex in the warp yarns and the weft yarns constituting the cylindrical fabric whose inside contacts blood is preferably not less than 50%, more preferably not less than 60%, still more preferably not less than 80%.

From the viewpoint of promoting settlement of vascular endothelial cells and increasing the cellular affinity, the single yarn diameter of the warp yarns and the weft yarns constituting the cylindrical fabric whose inside contacts blood is preferably 300 nm to 10 µm, more preferably 1 to 5 µm, still more preferably 3 µm. The single yarn diameter of the warp yarns and the weft yarns constituting the cylindrical fabric whose inside contacts blood was measured on a micrograph at a magnification of ×400.

The cover factor on the inner surface of the artificial blood vessel represents the extent of the gaps between the fibers of the cylindrical fabric whose inside contacts blood, that is, the packing density. The smaller the cover factor, the larger the gaps between the fibers. When the cover factor on the inner surface of the artificial blood vessel is too large, the packing density is high, and the flexibility is therefore lower than that of living blood vessels, resulting in not only hardening of the artificial blood vessel, but also unstable weaving performance. On the other hand, when the cover factor on the inner surface of the artificial blood vessel is too small, the sizes and the amount of the gaps between the fibers are large, and therefore the water permeability is high, and the amount of blood leakage is large. Accordingly, the cover factor on the inner surface of the artificial blood vessel is preferably 1800 to 4000, more preferably 2000 to 3000. The cover factor on the inner surface of the artificial blood vessel is a value calculated from the total fineness and the base fabric density of the multifilament yarns used as the warp yarns and the weft yarns, and is calculated according to Equation (1).

$$CF = (Dw \times 0.9)^{1/2} \times Nw + (Df \times 0.9)^{1/2} \times Nf \quad (1)$$

CF: cover factor on the inner surface of the artificial blood vessel
Dw: total fineness of the warp yarns (dtex)
Nw: base fabric density of the warp yarns (yarns/2.54 cm)
Df: total fineness of the weft yarns (dtex)
Nf: base fabric density of the weft yarns (yarns/2.54 cm)

The base fabric density was measured by cutting the prepared cylindrical fabric in the longitudinal direction, and then observing the inner surface on a photograph at a magnification of ×50 taken using a microscope manufactured by Keyence Corporation, VHX-2000.

A multifilament yarn of not less than 1.0 dtex is preferably contained as a warp yarn constituting at least one layer other than the cylindrical fabric whose inside contacts blood. When the single yarn fineness of the warp yarn constituting the at least one layer other than the cylindrical fabric whose inside contacts blood is too small, the mechanical strength of the artificial blood vessel is insufficient and, during long-term transplantation, deterioration of the strength may occur due to hydrolysis of the fibers constituting the artificial blood vessel, which is not preferred. On the other hand, when the single yarn fineness of the warp yarn constituting the at least one layer other than the cylindrical fabric whose inside contacts blood is too large, a kink is generated due to hardness of the artificial blood vessel against bending. That is, as the warp yarn constituting the at least one layer other than the cylindrical fabric whose inside contacts blood, a multifilament yarn having a single yarn fineness of 1.0 to 10.0 dtex is preferably contained. The single yarn fineness is more preferably 2.0 to 5.0 dtex. The at least one layer other than the cylindrical fabric whose inside contacts blood is preferably the outer-layer cylindrical fabric.

When the multifilament yarn of not less than 1.0 dtex to be used as a warp yarn constituting the at least one layer other than the cylindrical fabric whose inside contacts blood is exposed on the inner surface portion of the artificial blood vessel which contacts blood, the ratio of the multifilament yarn having a single yarn fineness of not more than 0.50 dtex as a warp yarn constituting the cylindrical fabric whose inside contacts blood, which promotes settlement of vascular endothelial cells, decreases and, moreover, gaps between fibers are likely to be generated so that the amount of blood leakage increases. In view of this, the percentage of exposure of the multifilament yarn of not less than 1.0 dtex on the inner surface is preferably not more than 20%, more preferably not more than 5%, still more preferably not more than 1%. The percentage of exposure (%) of the multifilament yarn of not less than 1.0 dtex on the inner surface means the ratio corresponding to the number of ridge portions where a multifilament yarn of not less than 1.0 dtex can be found among 100 ridge portions of warp yarns that are randomly selected by visual observation of the inner surface of the artificial blood vessel.

Further, a monofilament yarn is preferably contained as a weft yarn constituting at least one layer other than the cylindrical fabric whose inside contacts blood. When the single yarn fineness of the weft yarn constituting the at least one layer other than the cylindrical fabric whose inside contacts blood is too small, the shape and the elasticity of the artificial blood vessel cannot be maintained, and the kink resistance cannot be improved. On the other hand, when the single yarn fineness of the weft yarn constituting the at least one layer other than the cylindrical fabric whose inside contacts blood is too large, the artificial blood vessel is hard and, moreover, the weaving performance is unstable. Thus, depending on the type and the performance of the loom, the single yarn fineness is preferably 15.0 to 1000.0 dtex, more preferably 20.0 to 100.0 dtex. The at least one layer other than the cylindrical fabric whose inside contacts blood is preferably the outer-layer cylindrical fabric.

The antithrombogenicity means a property with which blood coagulation does not occur on a surface in contact with blood. For example, the antithrombogenicity means a property that inhibits blood coagulation that proceeds due to platelet aggregation, activation of blood coagulation factors represented by thrombin, and/or the like. The cellular affinity means a property with which vascular endothelial cells, present on the inner surface of living blood vessels and capable of inhibiting thrombus formation, are likely to be settled, leading to formation of the intima.

The antithrombogenic material means a material having antithrombogenicity. More specifically, an antithrombogenic material A, comprising an anionic compound containing a sulfur atom and having anticoagulant activity, and a cationic polymer; and an antithrombogenic material B, comprising the following three kinds of skeletal structures: a skeletal structure composed of a hydrophilic polymer, a skeletal structure composed of 4-(aminomethyl)benzenecarboxyimidamide or benzene amidine, and a skeletal structure composed of methoxybenzenesulfonic acid amide;

are used as the antithrombogenic material.

In the artificial blood vessel, the antithrombogenic material is bound to the inside of the cylindrical fabric whose inside contacts blood, to form the antithrombogenic material layer. In terms of the range of the thickness of this antithrombogenic material layer, when the layer is too thick, the microstructure composed of the warp yarns and the weft yarns constituting the cylindrical fabric whose inside contacts blood on the inner surface of the artificial blood vessel which contacts blood is destroyed, and therefore settlement of vascular endothelial cells is less likely to occur. On the other hand, in terms of the range of the thickness, when the layer is too thin, the binding amount of the antithrombogenic material is small so that the antithrombogenicity of interest required immediately after the transplantation cannot be obtained. That is, the range of the thickness of the antithrombogenic material layer bound to the cylindrical fabric whose inside contacts blood is preferably 1 to 600 nm, more preferably 5 to 500 nm, still more preferably 10 to 400 nm.

The thickness of the antithrombogenic material layer can be determined by, for example, using the later-described scanning transmission electron microscope (hereinafter referred to as "STEM"). The atomic distribution is observed in the vertical direction from the inner-layer side toward the outer-layer side using, as the start point, the inner surface as measured by STEM. The thickness of the antithrombogenic material layer means the distance from the start point to the end point of the range in which atoms derived from the antithrombogenic material layer are found. The thickness of the antithrombogenic material layer is measured as the mean of the values of the thickness at at least three points.

The inner surface as measured by STEM means the boundary between the acrylic resin or the like used to embed in the sample preparation before the measurement by STEM, and the inner surface including the inside of the cylindrical fabric whose inside contacts blood, and the antithrombogenic material layer.

Since the amount of blood leakage needs to be reduced, the artificial blood vessel is preferably composed of nonporous fibers. In addition, the antithrombogenic material is preferably present also in the outer-layer side, that is, in the depth direction, of the cylindrical fabric whose inside contacts blood. More specifically, when the position where atoms derived from the warp yarns and the weft yarns constituting the cylindrical fabric whose inside contacts blood are present, rather than the inner surface as measured by STEM, is used as the start point, and the atomic distribution in the cylindrical fabric whose inside contacts blood is observed toward the outer-layer side in the vertical direction, the distance from the start point to the end point of the range in which atoms derived from the antithrombogenic material layer are found is more preferably not less than 15 nm, that is, atoms derived from the antithrombogenic material are more preferably present for a distance of not less than 15 nm in the depth direction from the surface of the cylindrical fabric whose inside contacts blood. When the distance from the start point to the end point of the range in which atoms derived from the antithrombogenic material layer are found is less than 15 nm, the binding amount of the antithrombogenic material is small so that the antithrombogenicity of interest required immediately after the transplantation cannot be satisfied. On the other hand, the distance from the start point to the end point of the range in which atoms derived from the antithrombogenic material layer are found may exceed 200 nm. However, to allow the antithrombogenic material to be present in the outer-layer side, that is, in the depth direction, of the cylindrical fabric whose inside contacts blood, the fibers constituting the artificial blood vessel are moderately subjected to hydrolysis or oxidation treatment using an acid or an alkali, and an oxidizing agent. This may cause deterioration, leading to a decrease in mechanical properties such as the tensile strength of the artificial blood vessel. In view of this, the antithrombogenic material is preferably bound to the warp yarns and the weft yarns constituting the cylindrical fabric whose inside contacts blood such that the end point of the atoms derived from the antithrombogenic material is present at a position of 15 to 200 nm in the depth direction.

As described above, we discovered that settlement of vascular endothelial cells and formation of the intima can be promoted by maintaining the microstructure composed of the warp yarns and the weft yarns constituting the cylindrical fabric whose inside contacts blood on the inner surface of the artificial blood vessel which contacts blood, while binding the antithrombogenic material to the warp yarns and the weft yarns constituting the cylindrical fabric whose inside contacts blood such that an antithrombogenic material layer having an appropriate thickness is formed. We also discovered that, since the microstructure can be maintained while a sufficient binding amount of the antithrombogenic material can be achieved, the antithrombogenicity of interest required immediately after the transplantation can be obtained so that both the antithrombogenicity and the cellular affinity can be achieved.

More specifically, the thickness of the antithrombogenic material layer, and the distance from the start point to the end point of the range in which atoms derived from the antithrombogenic material layer are found when the position where the warp yarns and the weft yarns constituting the cylindrical fabric whose inside contacts blood are present is used as the start point, and the atomic distribution in the cylindrical fabric whose inside contacts blood is observed toward the outer-layer side in the vertical direction, can be confirmed by combination of, for example, STEM and X-ray photoelectron spectroscopy (hereinafter referred to as "XPS"). A STEM has detectors such as an energy dispersive X-ray spectrometer (hereinafter referred to as "EDX") and an electron energy-loss spectrometer (hereinafter referred to as "EELS"). Measurement conditions for the STEM are as follows.

Measurement Conditions

Apparatus: field emission transmission electron microscope JEM-2100F (manufactured by JEOL Ltd.)

EELS detector: GIF Tridiem (manufactured by GATAN, Inc.)

EDX detector: JED-2300T (manufactured by JEOL Ltd.)

Image acquisition: Digital Micrograph (manufactured by GATAN, Inc.)

Sample preparation: ultrathin sectioning (suspension using a copper microgrid; use of an acrylic resin as an embedding resin)

Acceleration voltage: 200 kV

Beam diameter: 0.7-nm diameter

Energy resolution: about 1.0 eV FWHM

The presence of each kind of atoms is judged based on whether a peak intensity derived from the atoms can be found in a spectrum obtained by STEM measurement after subtraction of the background.

The antithrombogenic material A is preferably an anionic compound containing a sulfur atom and having anticoagulant activity. The antithrombogenic material A preferably further contains a cationic polymer. More specifically, the antithrombogenic material A more preferably contains a cationic polymer containing, as a constituent monomer A, a compound selected from the group consisting of alkyleneimines, vinylamines, allylamines, lysine, protamine, and diallyldimethylammonium chloride.

Since these constituent monomers A have a cationic nitrogen atom, the polymer is cationic. On the other hand, the compound having anticoagulant activity and containing a sulfur atom is anionic. Therefore, the polymer and the compound can be ionically bound to each other. Examples of the anionic compound containing a sulfur atom and having anticoagulant activity include heparin and heparin derivatives, dextran sulfate, polyvinyl sulfonate, and polystyrene sulfonate. Heparin and heparin derivatives are more preferred. The heparin and heparin derivatives may be either purified or unpurified, and are not limited as long as they can inhibit blood coagulation reaction. Examples of the heparin and heparin derivatives include heparins clinically generally and widely used, unfractionated heparins, and low-molecular-weight heparins, as well as heparins having high affinity to antithrombin III. Specific examples of the heparin include "heparin sodium" (manufactured by Organon API Inc.).

Since the cationic polymer has a cationic property, it may exhibit hemolytic toxicity and/or the like. Therefore, elution of the cationic polymer into blood is not preferred. In view of this, the cationic polymer is preferably bound, more preferably covalently bound, to the warp yarns and the weft yarns constituting the cylindrical fabric whose inside contacts blood.

The cationic polymer may be either a homopolymer or a copolymer. When the cationic polymer is a copolymer, the copolymer may be any of a random copolymer, block copolymer, graft copolymer, and alternating copolymer. The cationic polymer is more preferably a block copolymer since, when the block copolymer has a block containing consecutive repeat units containing nitrogen atoms, the block portion interacts with the anionic compound containing a sulfur atom and having anticoagulant activity, to form strong ionic bonds.

The homopolymer means a macromolecular compound obtained by polymerization of a single kind of constituent monomers. The copolymer means a macromolecular compound obtained by copolymerization of two or more kinds of monomers. The block copolymer means a copolymer having a molecular structure in which at least two kinds of polymers having different repeat units are covalently bound to each other to form a longer chain. The block means each of the at least two kinds of polymers having different repeat units constituting the block copolymer.

The structure of the cationic polymer may be either linear or branched. The polymer is preferably branched since a branched polymer can form more stable ionic bonds at multiple positions with the anionic compound containing a sulfur atom and having anticoagulant activity.

The cationic polymer has at least one functional group selected from primary to tertiary amino groups and a quaternary ammonium group. In particular, the cationic polymer more preferably has a quaternary ammonium group rather than primary to tertiary amine groups since a quaternary ammonium group has stronger ionic interaction with the anionic compound containing a sulfur atom and having anticoagulant activity, and hence allows easier control of the elution rate of the anionic compound containing a sulfur atom and having anticoagulant activity.

The carbon numbers of the three alkyl groups constituting the quaternary ammonium group are not limited. However, when the carbon numbers are too large, hydrophobicity is high, and steric hindrance is enhanced so that the anionic compound containing a sulfur atom and having anticoagulant activity cannot effectively bind to the quaternary ammonium group by ionic bonding. Moreover, when the carbon number is too large, the polymer is more likely to show hemolytic toxicity so that the carbon number per alkyl group bound to the nitrogen atom constituting the quaternary ammonium group is preferably 1 to 12, more preferably 2 to 6. The carbon numbers of the three alkyl groups bound to the nitrogen atom constituting the quaternary ammonium group may be the same as or different from each other.

A polyalkyleneimine is preferably used as the cationic polymer since the amount of the anionic compound containing a sulfur atom and having anticoagulant activity adsorbed thereto by ionic interaction is large. Examples of the polyalkyleneimine include polyethyleneimines (hereinafter referred to as "PEI"), polypropyleneimines, and polybutyleneimines, as well as alkoxylated polyalkyleneimines. Among these, PEI is more preferred.

Specific examples of the PEI include "LUPASOL" (registered trademark) (manufactured by BASF), and "EPOMIN" (registered trademark) (manufactured by Nippon Shokubai Co., Ltd.). The PEI may be a copolymer with other monomers, or may be a modified body, as long as the desired effect is not deteriorated. The modified body means a cationic polymer having the same monomer A repeat units constituting it, but has partially undergone, for example, radical decomposition or recombination due to the later-mentioned radiation irradiation.

In the cationic polymer, constituent monomers used to form the copolymer other than alkyleneimines, vinylamines, allylamines, lysine, protamine, and diallyldimethylammonium chloride are not limited, and examples of the constituent monomers include constituent monomers B such as ethylene glycol, propylene glycol, vinylpyrrolidone, vinyl alcohol, vinylcaprolactam, vinyl acetate, styrene, methyl methacrylate, hydroxyethyl methacrylate, and siloxane. When the weight of the constituent monomers B is too high, the ionic bonding between the cationic polymer and the anionic compound containing a sulfur atom and having anticoagulant activity is weak. Therefore, the weight of the constituent monomers B with respect to the total weight of the cationic polymer is preferably not more than 10 wt %.

When the weight average molecular weight of the cationic polymer is too low, and lower than the molecular weight of the anionic compound containing a sulfur atom and having anticoagulant activity, stable ionic bonds cannot be formed so that the antithrombogenicity of interest is less likely to be obtained. On the other hand, when the weight average molecular weight of the cationic polymer is too high, the anionic compound containing a sulfur atom and having anticoagulant activity is included inside the cationic polymer, resulting in embedding of the antithrombogenic material. Thus, the weight average molecular weight of the cationic polymer is preferably 600 to 2,000,000, more preferably 1000 to 1,500,000, still more preferably 10,000 to 1,000,000. The weight average molecular weight of the cationic polymer can be measured by, for example, gel permeation chromatography or the light scattering method.

To achieve both the antithrombogenicity and the cellular affinity by the presence of the anionic compound containing a sulfur atom and having anticoagulant activity, while maintaining the microstructure composed of the warp yarns and the weft yarns constituting the cylindrical fabric whose inside contacts blood and containing a multifilament yarn having a single yarn fineness of not more than 0.50 dtex, we discovered that there is a preferred value of the abundance ratio of sulfur atoms to the abundance of total atoms on the inner surface as measured by XPS. The abundance ratio of atoms is expressed as "atomic percent", and the atomic percent means the abundance ratio of a particular kind of atoms to the abundance of total atoms, which is taken as 100, in terms of the number of atoms.

That is, the abundance ratio of sulfur atoms to the abundance of total atoms on the inner surface as measured by XPS is preferably 3.0 to 6.0 atomic percent, more preferably 3.2 to 5.5 atomic percent, still more preferably 3.5 to 5.0 atomic percent. When the abundance ratio of sulfur atoms to the abundance of total atoms is less than 3.0 atomic percent, the binding amount of the anionic compound containing a sulfur atom and having anticoagulant activity is small and, therefore, the antithrombogenicity of interest required immediately after the transplantation of the artificial blood vessel is less likely to be obtained. On the other hand, when the abundance ratio of sulfur atoms to the abundance of total atoms is higher than 6.0 atomic percent, the binding amount of the anionic compound containing a sulfur atom and having anticoagulant activity is sufficient, and the antithrombogenicity of interest can therefore be obtained, but the amount of the cationic polymer covalently bound to the warp yarns and the weft yarns constituting the cylindrical fabric whose inside contacts blood, which cationic polymer is used for allowing the ionic bonding, needs to be large. Moreover, as elution of the anionic compound containing a sulfur atom and having anticoagulant activity proceeds, the exposed cationic polymer may exhibit hemolytic toxicity and/or the like, which is not preferred.

When the abundance ratio of sulfur atoms to the abundance of total atoms is not more than 6.0 atomic percent, the binding amount of the anionic compound containing a sulfur atom and having anticoagulant activity is appropriate so that settlement of vascular endothelial cells can be promoted.

More specifically, the abundance ratio of sulfur atoms to the abundance of total atoms on the inner surface as measured by XPS can be determined by XPS.

Measurement Conditions
  Apparatus: ESCALAB 220iXL (manufactured by VG Scientific)
  Excitation X-ray: monochromatic A1K al, 2 ray (1486.6 eV)
  X-ray diameter: 1 mm
  X-electron escape angle: 90° (the angle of the detector with respect to the surface of the antithrombogenic material)

The inner surface as measured by X-ray photoelectron spectroscopy (XPS) means the portion from the measurement surface to a depth of 10 nm as detected under the measurement conditions in XPS wherein the X-electron escape angle, that is, the angle of the detector with respect to the inner surface of the artificial blood vessel to which the antithrombogenic material and the cylindrical fabric are bound, is 90°. The cylindrical fabric may or may not contain sulfur atoms.

By radiating X-ray to the inner surface of the artificial blood vessel, and measuring the energy of photoelectrons generated therefrom, the binding energy values of bound electrons in the substance can be obtained. From the binding energy values, information on the atoms on the inner surface as measured by XPS can be obtained, and, from the energy shift of the peak at each binding energy value, information on the valence and the binding state can be obtained. In addition, by using the area ratio of each peak, quantification, that is, calculation of the abundance ratios of various atoms, valences, and binding states, is possible.

More specifically, the S2p peak, which indicates the presence of sulfur atoms, appears near a binding energy value of 161 eV to 170 eV. We discovered that the area ratio of the S2p peak in the whole peak area is preferably 3.0 to 6.0 atomic percent. In the calculation of the abundance ratio of sulfur atoms to the abundance of total atoms, the obtained value is rounded to one decimal place.

Similarly, we discovered that there is a preferred value of the abundance ratio of nitrogen atoms to the abundance of total atoms on the inner surface as measured by XPS. That is, the abundance ratio of nitrogen atoms to the abundance of total atoms on the inner surface as measured by XPS is preferably 6.0 to 12.0 atomic percent, more preferably 7.0 to 12.0 atomic percent, still more preferably 7.5 to 11.0 atomic percent, still more preferably 8.0 to 10.0 atomic percent. When the abundance ratio of nitrogen atoms to the abundance of total atoms is less than 6.0 atomic percent, the amount of the cationic polymer bound to the cylindrical fabric whose inside contacts blood is small so that the microstructure composed of the warp yarns and the weft yarns containing a multifilament yarn having a single yarn fineness of not more than 0.50 dtex can be maintained. However, since the amount of the anionic compound containing a sulfur atom and having anticoagulant activity which is ionically bound to the cationic polymer is small in such cases, the antithrombogenicity of interest required immediately after the transplantation is less likely to be obtained. On the other hand, when the abundance ratio of nitrogen atoms to the abundance of total atoms is higher than 12.0 atomic percent, the amount of the cationic polymer bound to the cylindrical fabric whose inside contacts blood is large so that the anionic compound containing a sulfur atom and having anticoagulant activity bound to the cationic polymer by ionic bonding is present in a sufficient amount. However, we found that, as elution of the anionic compound containing a sulfur atom and having anticoagulant activity proceeds, a large amount of the cationic polymer is exposed to show hemolytic toxicity.

When the abundance ratio of nitrogen atoms to the abundance of total atoms is not more than 12.0 atomic percent, the binding amount of the anionic compound containing a sulfur atom and having anticoagulant activity is appropriate so that settlement of vascular endothelial cells is promoted. To achieve both the antithrombogenicity and the cellular affinity, the abundance ratio of nitrogen atoms to the abundance of total atoms is preferably 6.0 to 12.0 atomic percent, more preferably 6.0 to 9.5 atomic percent, still more preferably 8.0 to 9.5 atomic percent.

More specifically, the N1s peak, which indicates the presence of nitrogen atoms, appears near a binding energy value of 396 eV to 403 eV. We discovered that the area ratio of the N1s peak in the whole peak area is preferably 7.0 to 12.0 atomic percent. The N1s peak can be mainly split into the n1 component (near 399 eV), which is attributed to carbon-nitrogen (hereinafter referred to as "C—N") bonds; and the n2 component (near 401 to 402 eV), which is attributed to ammonium salt, C—N(structure different from n1), and/or nitrogen oxide (hereinafter referred to as "NO"). The abundance ratio of each split peak component can be calculated according to Equation (2). In this calculation, the abundance ratio of nitrogen atoms to the abundance of total atoms, and the abundance ratio of each split peak component, are rounded to one decimal place.

$$\text{Split}_{ratio} = \text{N1s}_{ratio} \times (\text{Split}_{percent}/100) \qquad (2)$$

$\text{Split}_{ratio}$: abundance ratio of each split peak component (%)

$\text{N1s}_{ratio}$: abundance ratio of nitrogen atoms to the abundance of total atoms (%)

$\text{Split}_{percent}$: abundance ratio of each split peak component in the N1s peak (%)

The n2 component, which is attributed to NO, obtained by splitting the N1s peak indicates the presence of quaternary ammonium groups. We discovered that the abundance ratio of the n2 component in the total component of the N1s peak, that is, $\text{Split}_{percent}$ (n2), is preferably 20 to 70 atomic percent, more preferably 25 to 65 atomic percent, still more preferably 30 to 60 atomic percent. When $\text{Split}_{percent}$ (n2) is less than 20 atomic percent, the abundance of quaternary ammonium groups is low. Therefore, the ionic interaction with the anionic compound containing a sulfur atom and having anticoagulant activity is weak, and the antithrombogenicity of interest required immediately after the transplantation of the artificial blood vessel is less likely to be obtained because of high elution rate. On the other hand, when $\text{Split}_{percent}$ (n2) is higher than 70 atomic percent, the ionic interaction with the anionic compound containing a sulfur atom and having anticoagulant activity is too strong. In such cases, because of a decrease in the degree of freedom due to formation of ionic complexes, it is impossible to maintain a high anticoagulant activity for a long period, and the elution rate tends be low. Because of the above reasons, the abundance ratio of the n2 component, that is, $\text{Split}_{ratio}$ (n2), which is calculated according to Equation (2), is preferably 1.4 to 8.4 atomic percent, more preferably 1.8 to 7.2 atomic percent, still more preferably 2.4 to 6.0 atomic percent.

The C1s peak, which indicates the presence of carbon atoms, appears near a binding energy value of 282 to 292 eV. The C1s peak can be mainly split into the c1 component (near 285 eV), which is attributed to carbon-hydrogen (hereinafter referred to as "CHx") bonds suggesting the presence of a saturated hydrocarbon(s) and/or the like, to carbon-carbon (hereinafter referred to as "C—C") bonds, and/or to carbon=carbon (hereinafter referred to as "C=C") bonds; the c2 component (near 286 eV), which is attributed to carbon-oxygen (hereinafter referred to as "C—O") bonds suggesting the presence of an ether(s) and/or hydroxyl groups, and/or to carbon-nitrogen (hereinafter referred to as "C—N") bonds; the c3 component (near 287 to 288 eV), which is attributed to carbon=oxygen (hereinafter referred to as "C=O") bonds suggesting the presence of carbonyl groups; the c4 component (near 288 to 289 eV), which is attributed to oxygen=carbon-oxygen (hereinafter referred to as "O=C—O") bonds suggesting the presence of ester groups and/or carboxyl groups; and the c5 component (near 290 to 292 eV), which is attributed to π-π* satellite peak (hereinafter referred to as "π-π") bonds suggesting the presence of a conjugated system(s) such as benzene rings. The abundance ratio of each split peak component can be calculated according to Equation (3). In this calculation, the abundance ratio of carbon atoms to the abundance of total atoms, and the abundance ratio of each split peak component, are rounded to one decimal place.

$$\text{Split}_{ratio} = \text{C1s}_{ratio} \times (\text{Split}_{percent}/100) \qquad (3)$$

$\text{Split}_{ratio}$: abundance ratio of each split peak component (%)

$\text{C1s}_{ratio}$: abundance ratio of carbon atoms to the abundance of total atoms (%)

$\text{Split}_{percent}$: abundance ratio of each split peak component in the C1s peak (%)

The c3 component, which is attributed to C=O bonds, obtained by splitting the C1s peak indicates the presence of amide groups. We discovered that the abundance ratio of the c3 component in the total component of the C1s peak, that is, the abundance ratio of amide groups, is preferably not less than 2.0 atomic percent, more preferably not less than 3.0 atomic percent. When the abundance ratio of the amide groups is less than 2.0 atomic percent, the number of covalent bonds due to amide bonds between the cationic polymer and the cylindrical fabric whose inside contacts blood is small and, therefore, the binding amount of the cationic polymer is small. Moreover, since the state of ionic bonding between the cationic polymer and the anionic compound containing a sulfur atom and having anticoagulant activity is poor, the antithrombogenicity of interest is less likely to be obtained.

The antithrombogenic material B preferably contains the following three kinds of skeletal structures: a skeletal structure composed of a hydrophilic polymer, a skeletal structure composed of 4-(aminomethyl)benzenecarboxyimidamide or benzene amidine, and a skeletal structure composed of methoxybenzenesulfonic acid amide. More specifically, the hydrophilic polymer more preferably contains, as a constituent monomer B, a compound selected from the group consisting of ethylene glycol, propylene glycol, vinylpyrrolidone, vinyl alcohol, vinylcaprolactam, vinyl acetate, styrene, methyl methacrylate, hydroxyethyl methacrylate, and siloxane.

Each of the three kinds of skeletal structures described above may be contained in a separate compound, or at least two kinds of the skeletal structures may be bound to a compound by covalent bonding or ionic bonding. In the artificial blood vessel, from the viewpoint of achieving both the antithrombogenicity and the cellular affinity, it is more preferred to use, as the antithrombogenic material B, a compound containing all of the skeletal structure composed of a hydrophilic polymer, the skeletal structure composed of 4-(aminomethyl)benzenecarboxyimidamide or benzene amidine, and the skeletal structure composed of methoxybenzenesulfonic acid amide.

At least one of the three kinds of skeletal structures described above preferably contains a functional group selected from the group consisting of, for example, hydroxyl, thiol, amino, carboxyl, aldehyde, isocyanate, and thioisocyanate, more preferably contains amino or carboxyl, still more preferably contains amino. The functional group is preferably contained in the skeletal structure composed of a hydrophilic polymer, more preferably present at the terminus of the skeletal structure composed of a hydrophilic polymer. The warp yarns and the weft yarns constituting the cylindrical fabric whose inside contacts blood can be covalently bound to the three kinds of skeletal structures through disulfide bonds, amide bonds, ester bonds, urethane bonds, bonds formed by condensation reaction, and/or the like, using a functional group(s) selected from the group consisting of hydroxyl, thiol, amino, carboxyl, aldehyde, isocyanate, and thioisocyanate.

The reactive functional group(s) is/are given to the antithrombogenic material to allow covalent bonding of the antithrombogenic material to the warp yarns and the weft yarns constituting the cylindrical fabric whose inside contacts blood. Therefore, the covalent bonding can be carried out without use of a method such as radiation irradiation. When the covalent bonding is carried out by radiation irradiation or the like as described in WO 08/032758 and WO 12/176861, the skeletal structure composed of 4-(aminomethyl)benzenecarboxyimidamide or benzene amidine, and the skeletal structure composed of methoxybenzenesulfonic acid amide, generate highly reactive radicals due to absorption of high energy of the radiation. Reaction of the radicals with arbitrary sites in the compound causes changes in the skeletal structures, mainly leading to a decrease in antithrombin activation capacity.

To achieve both the antithrombogenicity and the cellular affinity in the antithrombogenic material B using a compound having antithrombogenicity other than heparin or heparin derivatives, especially to further increase the antiplatelet adhesion capacity associated with the antithrombogenicity, we discovered that the skeletal structure composed of a hydrophilic polymer is important.

The skeletal structure composed of a hydrophilic polymer means a skeletal structure composed of a polymer having a hydrophilic functional group and having solubility in water. The hydrophilic polymer may be a copolymer with other monomers, or may be a modified body as long as the desired effect is not deteriorated.

The skeletal structure composed of a hydrophilic polymer may be either a homopolymer or a copolymer as long as the constituent monomer B described above is used. When the hydrophilic polymer is a copolymer, the copolymer may be any of a random copolymer, block copolymer, graft copolymer, and alternating copolymer. The skeletal structure composed of a hydrophilic polymer may be either linear or branched.

In the achievement of both the antithrombogenicity and the cellular affinity in the antithrombogenic material B using a compound having antithrombogenicity other than heparin or heparin derivatives, especially to further increase the antithrombin activation capacity associated with the antithrombogenicity, we discovered that the skeletal structure composed of 4-(aminomethyl)benzenecarboxyimidamide or benzene amidine, and the skeletal structure composed of methoxybenzenesulfonic acid amide, are important.

The skeletal structure composed of 4-(aminomethyl)benzenecarboxyimidamide is a skeletal structure shown in General Formula (V); the skeletal structure composed of benzene amidine is a skeletal structure shown in General Formula (VI); and the skeletal structure composed of methoxybenzenesulfonic acid amide is a skeletal structure shown in General Formula (VII).

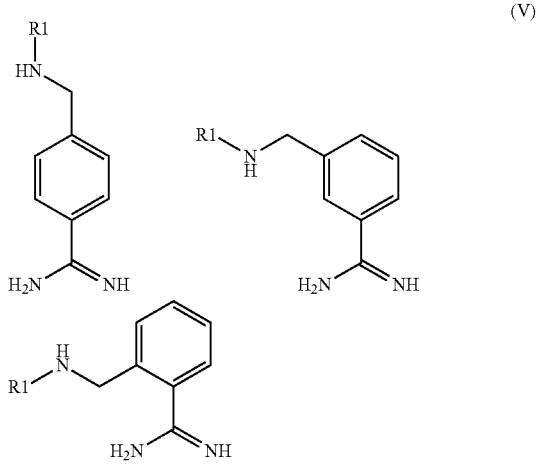

(V)

wherein R1 represents a moiety linked to another skeletal structure.

(VI)

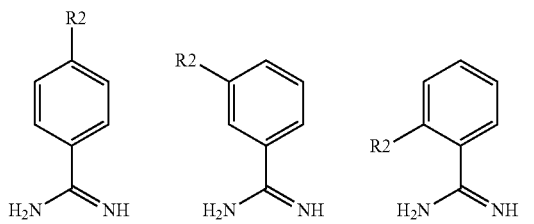

wherein R2 represents a moiety linked to another skeletal structure.

(VII)

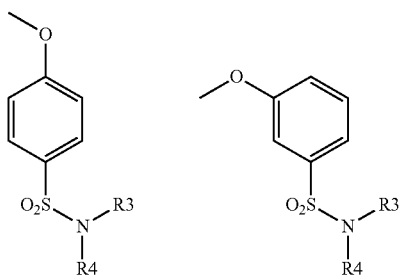

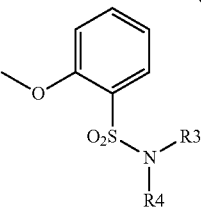

wherein each of R3 and R4 represents a moiety linked to another skeletal structure.

The compound containing all of the three kinds of structures, that is, the skeletal structure composed of a hydrophilic polymer, the skeletal structure composed of 4-(aminomethyl)benzenecarboxyimidamide or benzene amidine, and the skeletal structure composed of methoxybenzenesulfonic acid amide, is especially preferably any of the compounds represented by General Formulae (I) to (IV). In these General Formulae, X is preferably amino or carboxyl. X is more preferably amino.

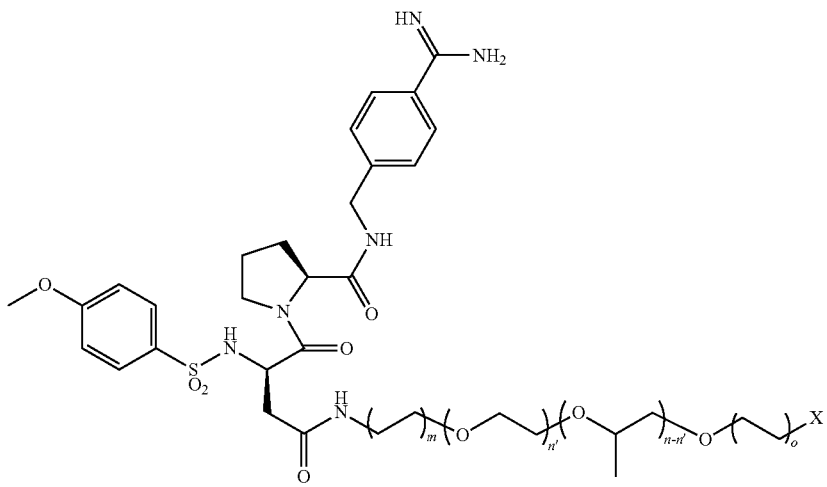

(IV)

wherein m and o each represent an integer of 0 to 4; n represents an integer of 3 to 1000, and n' represents an integer of 3 to 1000, with the proviso that n>n'; and X represents a functional group selected from the group consisting of hydroxyl, thiol, amino, carboxyl, aldehyde, isocyanate, and thioisocyanate.

We discovered that, although X in the formulae described above may be contained in any of the three kinds of skeletal structures, a high and long-lasting antithrombogenicity can be obtained when the skeletal structure composed of a hydrophilic polymer, which has anti-platelet adhesion capacity, is present in the side in contact with the cylindrical fabric whose inside contacts blood, to which the above compound is bound, and the skeletal structure composed of 4-(aminomethyl)benzenecarboxyimidamide or benzene amidine and the skeletal structure composed of methoxybenzenesulfonic acid amide, which have antithrombin activation capacity, are present in the side in contact with blood, since the latter skeletal structures have higher thrombin capture capacity in such cases. That is, the reactive functional group (X in the formulae described above) to be covalently bound to the warp yarns and the weft yarns constituting the cylindrical fabric whose inside contacts blood is preferably contained in the skeletal structure composed of a hydrophilic polymer, more preferably present at the terminus of the skeletal structure composed of a hydrophilic polymer. The warp yarns and the weft yarns constituting the cylindrical fabric whose inside contacts blood can be covalently bound to the compound in the antithrombogenic material through disulfide bonds, amide bonds, ester bonds, urethane bonds, bonds formed by condensation reaction, and/or the like, using the reactive functional group X in the Formulae.

We discovered that, more preferably, for maintenance of a high antithrombogenicity for a longer period, the antithrombogenic material B contains a betaine compound, and the betaine compound is covalently bound to the warp yarns and the weft yarns constituting the cylindrical fabric whose inside contacts blood, or to the antithrombogenic material B.

The betaine compound means a compound which has a positive charge and a negative charge at positions that are not adjacent to each other in a single molecule, wherein no dissociable hydrogen atom is bound to the atom having the positive charge, and the molecule as a whole does not have a charge; or a salt thereof. The compound is not limited as long as it contains a betaine compound in a part thereof. The betaine compound is preferably carboxybetaine, sulfobetaine, or phosphobetaine, more preferably carboxybetaine or sulfobetaine represented by General Formula (VIII) or (IX). X in General Formulae (VIII) and (IX) is preferably amino or carboxyl. X is more preferably amino.

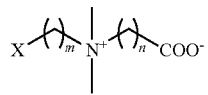

(VIII)

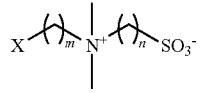

(IX)

wherein n represents any of 1 to 4; m represents an integer of 2 to 4; n' represents an integer of 2 to 4; m' represents an integer of 2 to 4; and X represents a functional group selected from the group consisting of hydroxyl, thiol, amino, carboxyl, aldehyde, isocyanate, and thioisocyanate.

In an artificial blood vessel to which an antithrombogenic material B using a compound having antithrombogenicity other than heparin or heparin derivatives is bound, the presence of the skeletal structure composed of a hydrophilic polymer, the skeletal structure composed of 4-(aminomethyl)benzenecarboxyimidamide or benzene amidine, and the skeletal structure composed of methoxybenzenesulfonic acid amide, on the innermost surface as measured by time-of-flight secondary ion mass spectrometry (hereinafter referred to as "TOF-SIMS") can be determined by TOF-SIMS.

Measurement Conditions

Apparatus: TOF.SIMS 5 (manufactured by ION-TOF GmbH)
  Primary ion species: $Bi_3^{++}$
  Secondary ion polarity: positive and negative
  Mass range (m/z): 0 to 1500
  Raster size: 300 μm×300 μm
  Pixel number (each side): 256 pixels
  Post-acceleration: 10 kV Measured degree of vacuum (before sample injection): $4\times10^{-7}$ Mpa Primary ion acceleration voltage: 25 kV Pulse width: 10.5 ns Bunching: Yes (high mass resolution measurement)

Charge neutralization: Yes

The "innermost surface as measured by TOF-SIMS" means the portion from the measurement surface to a depth of 1 to 3 nm under the measurement conditions in TOF-SIMS.

Pulsed primary ions are radiated to the innermost surface placed in an ultrahigh vacuum, and then secondary ions released from the innermost surface as measured by TOF-SIMS, having a certain amount of kinetic energy, are introduced to the time-of-flight mass spectrometer. Since a mass spectrum is obtained according to the mass of the secondary ions, organic substances and inorganic substances present on the innermost surface as measured by TOF-SIMS can be identified, and information on the abundance of each substance can be obtained based on its peak intensity.

More specifically, the skeletal structure composed of ethylene glycol or propylene glycol on the innermost surface as measured by TOF-SIMS can be confirmed based on at least one kind of peak selected from the group consisting of the $^{45}C_2H_5O^+$ peak, $^{59}C_3H_7O^+$ peak, $^{73}C_3H_5O_2^+$ peak, and $^{87}C_4H_7O_2^+$ peak of positive secondary ions found in TOF-SIMS.

The skeletal structure composed of 4-(aminomethyl)benzenecarboxyimidamide on the innermost surface as measured by TOF-SIMS can be confirmed based on at least one kind of peak selected from the group consisting of the $^{106}C_7H_8N^+$ peak, $^{117}C_7H_5N_2^+$ peak, $^{134}C_8H_{10}N_2^+$ peak, and $^{148}C_8H_{10}N_3^+$ peak of positive secondary ions, and the $^{119}C_7H_7N_2^-$ peak of negative secondary ions, found in TOF-SIMS. The skeletal structure composed of benzene amidine can be confirmed based on the $^{119}C_7H_7N_2^-$ peak of negative secondary ions found in TOF-SIMS. The skeletal structure composed of methoxybenzenesulfonic acid amide can be confirmed based on at least one kind of peak selected from the group consisting of the $^{117}C_7H_7SO_3^+$ peak of positive secondary ions, and the $^{64}SO_2^-$ peak, $^{171}C_7H_7SO_3^-$ peak, $^{186}C_7H_8SNO_3^-$ peak, and $^{212}C_9H_{10}SNO_3^-$ peak of negative secondary ions.

The presence of the betaine compound on the innermost surface as measured by TOF-SIMS can be confirmed based on at least one kind of peak selected from the group consisting of the $^{94}CH_2SO_3^-$ peak, $^{150}C_4H_8NSO_3^-$ peak, and $^{166}C_5H_{12}NSO_3^-$ peak of negative secondary ions found in TOF-SIMS.

For example, when the later-described cationic polymer is PEI, the presence of the PEI on the innermost surface can be confirmed based on at least one kind of peak selected from the group consisting of the $^{18}NH_4^+$ peak, $^{28}CH_2N^+$ peak, $^{43}CH_3N_2^+$ peak, and $^{70}C_4H_8N^+$ peak of positive secondary ions, and the $^{26}CN^-$ peak and $^{42}CNO^-$ peak of negative secondary ions, found in TOF-SIMS.

For example, when the later-described anionic polymer is polyacrylic acid (hereinafter referred to as "PAA"), the presence of the PAA on the innermost surface can be confirmed based on the $^{71}C_3H_3O_2^-$ peak of negative secondary ions found in TOF-SIMS.

For example, when the multifilament yarn of the artificial blood vessel is polyethylene terephthalate, the presence of the polyethylene terephthalate can be confirmed based on at least one kind of peak selected from the group consisting of the $^{76}C_6H_4^+$ peak, $^{104}C_7H_4NO^+$ peak, $^{105}C_7H_5O^+$ peak, and $^{149}C_8H_5O_3^+$ peak of positive secondary ions, and the $^{76}C_6N_4^-$ peak, $^{120}C_7H_4O_2^-$ peak, $^{121}C_7H_5O_2^-$ peak, $^{147}C_9H_7O_2^-$ peak, and $^{165}C_8H_5O_4^-$ peak of negative secondary ions, found in TOF-SIMS.

When the anionic polymer is PAA, there are preferred ranges of the abundance ratios of the skeletal structure composed of 4-(aminomethyl)benzenecarboxyimidamide or benzene amidine, and the skeletal structure composed of methoxybenzenesulfonic acid amide, to PAA on the innermost surface. When the presence of PAA is confirmed based on the $^{71}C_3H_3O_2^-$ peak of negative secondary ions found in TOF-SIMS, and the presence of the skeletal structure composed of 4-(aminomethyl)benzenecarboxyimidamide or benzene amidine is confirmed based on the $^{119}C_7H_7N_2^-$ peak of negative secondary ions found in TOF-SIMS, the peak ratio of $^{119}C_7H_7N_2^-$ peak/$^{71}C_3H_3O_2^-$ peak is preferably not less than 0.05. When the presence of PAA is confirmed based on the $^{71}C_3H_3O_2^-$ peak of negative secondary ions found in TOF-SIMS, and the presence of the skeletal structure composed of methoxybenzenesulfonic acid amide is confirmed based on the $^{64}SO_2^-$ peak, $^{171}C_7H_7SO_3^-$ peak, and $^{186}C_7H_8SNO_3^-$ peak of negative secondary ions found in TOF-SIMS, the peak ratio of $^{64}SO_2^-$ peak/$^{71}C_3H_3O_2^-$ peak is preferably not less than 0.6; the peak ratio of $^{171}C_7H_7SO_3^-$ peak/$^{71}C_3H_3O_2^-$ peak is preferably not less than 1.1; and the peak ratio of $^{186}C_7H_8SNO_3^-$ peak/$^{71}C_3H_3O_2^-$ peak is preferably not less than 0.5.

We achieved both the antithrombogenicity and the cellular affinity while suppressing elution of the compound when the antithrombogenic material B is used for the artificial blood vessel. As a result, we discovered that there is a preferred value of the abundance ratio of the c3 split peak component, which is attributed to C=O bonds and suggests the presence of carbonyl groups, to the C1s peak, that indicates the presence of carbon atoms, on the inner surface as measured by XPS.

That is, we discovered that the abundance ratio of the c3 split peak component to the total C1s peak component on the inner surface as measured by XPS is preferably not less than 1.0 atomic percent, more preferably not less than 2.0 atomic percent, still more preferably not less than 3.0 atomic percent. When the abundance ratio of the c3 split peak component to the total C1s peak component on the inner surface as measured by XPS is not less than 1.0 atomic percent, the antithrombogenic material B bound to the cylindrical fabric whose inside contacts blood is present in a sufficient amount so that a higher and longer-lasting antithrombogenicity can be obtained compared to when the antithrombogenic material is covalently bound by radiation irradiation as in WO 08/032758 and WO 12/176861. When the abundance ratio of the c3 split peak component to the total C1s peak component on the inner surface as measured by XPS is less than 1.0 atomic percent, the number of covalent bonds due to carbonyl-derived amide bonds between the antithrombogenic material B, and the warp yarns and the weft yarns constituting the cylindrical fabric whose inside contacts blood, is small and, therefore, the binding amount of the antithrombogenic material B is small so that the antithrombogenicity of interest is less likely to be obtained.

We discovered that, when the antithrombogenic material B is used for the artificial blood vessel, the abundance ratio of nitrogen atoms to the abundance of total atoms according to the N1s peak, which indicates the presence of nitrogen atoms on the inner surface as measured by XPS, is preferably 1.0 to 12.0 atomic percent, more preferably 2.0 to 11.0 atomic percent, still more preferably 3.0 to 10.0 atomic percent.

When the number average molecular weight of the skeletal structure composed of a hydrophilic polymer in the antithrombogenic material B is too low, the anti-platelet adhesion capacity is low so that the antithrombogenicity of interest required immediately after the transplantation of the artificial blood vessel is less likely to be obtained. On the other hand, when the number average molecular weight of the skeletal structure composed of a hydrophilic polymer is too high, the anti-platelet adhesion capacity is high, but the antithrombogenicity of interest is less likely to be obtained since the portion which exhibits the antithrombin activation capacity is included in the inside. Accordingly, the number average molecular weight of the skeletal structure composed of a hydrophilic polymer is preferably 1500 to 20,000, more preferably 2000 to 10,000.

The antithrombogenic material B containing the following three kinds of skeletal structures: a skeletal structure composed of a hydrophilic polymer containing, as a constituent monomer, a compound selected from the group consisting of ethylene glycol, propylene glycol, vinylpyrrolidone, vinyl alcohol, vinylcaprolactam, vinyl acetate, styrene, methyl methacrylate, hydroxyethyl methacrylate, and siloxane; a skeletal structure composed of 4-(aminomethyl)benzenecarboxyimidamide or benzene amidine; and a skeletal structure composed of methoxybenzenesulfonic acid amide; may further contain the cationic polymer described above.

The antithrombogenic materials, that is, the antithrombogenic material A and the antithrombogenic material B, preferably further comprise: an anionic polymer containing, as a constituent monomer, a compound selected from the group consisting of acrylic acid, methacrylic acid, α-glutamic acid, γ-glutamic acid, and aspartic acid; or an anionic compound selected from the group consisting of dicarboxylic acids such as oxalic acid, malonic acid, succinic acid, fumaric acid, glutaric acid, adipic acid, pimelic acid, suberic acid, azelaic acid, sebacic acid, malic acid, tartaric acid, and dodecanedioic acid; and citric acid.

The anionic polymer is preferably, but does not necessarily need to be, PAA, polymethacrylic acid, poly(α-glutamic acid), poly(γ-glutamic acid), or polyaspartic acid since, when the weight ratio of anionic functional groups is high, a larger amount of the polymer can be bound to the warp yarns and the weft yarns constituting the cylindrical fabric whose inside contacts blood, or to another antithrombogenic material. The anionic polymer is more preferably PAA.

Specific examples of the PAA include "polyacrylic acid" (manufactured by Wako Pure Chemical Industries, Ltd.). The PAA may be a copolymer with other monomers, or may be a modified body as long as the desired effect is not deteriorated.

The anionic polymer may, but does not necessarily need to, form a copolymer with monomers other than anionic monomers. Examples of such monomers include constituent monomers B such as ethylene glycol, propylene glycol, vinylpyrrolidone, vinyl alcohol, vinylcaprolactam, vinyl acetate, styrene, methyl methacrylate, hydroxyethyl methacrylate, and siloxane. The amount of the constituent monomers B forming the copolymer with the anionic polymer, other than anionic monomers, is preferably not more than 10 wt % since, when the amount of the constituent monomers B is too large, the amount of the copolymer bound to the cylindrical fabric whose inside contacts blood, or to another antithrombogenic material, is small.

From the viewpoint of safety and the like, elution of the anionic polymer into blood is not preferred. Therefore, the anionic polymer is preferably bound, more preferably covalently bound, to the warp yarns and the weft yarns constituting the cylindrical fabric whose inside contacts blood.

The cationic polymer may be either a homopolymer or a copolymer. When the anionic polymer is a copolymer, the copolymer may be any of a random copolymer, block copolymer, graft copolymer, and alternating copolymer.

In the anionic polymer, constituent monomers used to form the copolymer other than acrylic acid, methacrylic acid, α-glutamic acid, γ-glutamic acid, and aspartic acid are not limited, and examples of the constituent monomers include constituent monomers B such as ethylene glycol, propylene glycol, vinylpyrrolidone, vinyl alcohol, vinylcaprolactam, vinyl acetate, styrene, methyl methacrylate, hydroxyethyl methacrylate, and siloxane. When the weight of the constituent monomers B is too high, the number of reaction sites for binding to the warp yarns and the weft yarns constituting the cylindrical fabric whose inside contacts blood, or to another antithrombogenic material, is small. Accordingly, the weight of the constituent monomers B with respect to the total weight of the anionic polymer is preferably not more than 10 wt %.

The anionic compound is preferably, but does not necessarily need to be, oxalic acid, malonic acid, succinic acid, fumaric acid, glutaric acid, adipic acid, pimelic acid, suberic acid, azelaic acid, sebacic acid, malic acid, tartaric acid, or citric acid since, when the weight ratio of anionic functional groups is high, a larger amount of the compound can be bound to the cylindrical fabric whose inside contacts blood, or to another antithrombogenic material. The anionic compound is more preferably succinic acid.

When the weight average molecular weight of the anionic polymer is too small, the amount of the polymer bound to the cylindrical fabric whose inside contacts blood, or to another antithrombogenic material is small. It is therefore difficult to obtain a high and long-lasting antithrombogenicity. On the other hand, when the weight average molecular weight of the anionic polymer is too high, the antithrombogenic material is included in the inside. Therefore, the number average molecular weight of the anionic polymer is preferably 600 to 2,000,000, more preferably 10,000 to 1,000,000.

Various organic fibers may be used as the fiber to be used for the cylindrical fabric, especially as the multifilament yarn. From the viewpoint of water absorbability and resistance to deterioration, the fiber is preferably a polyester fiber. Examples of the polyester fiber include fibers composed of polyethylene terephthalate, polybutylene terephthalate or the like. The fiber may be composed of a copolymerized polyester prepared by copolymerization of polyethylene terephthalate, polybutylene terephthalate, or the like with an aliphatic dicarboxylic acid such as isophthalic acid, 5-sodium sulfoisophthalate, or adipic acid as an acid component. The fiber constituting the multifilament yarns and the fiber constituting the warp yarns and the weft yarns may be the same as or different from each other, and an appropriate combination of the fibers may be used.

Examples of looms which may be used include water jet looms, air-jet looms, rapier looms, and shuttle looms. In particular, a shuttle loom is preferably used since it has an excellent weaving performance for cylindrical shapes, and is capable of producing a uniform cylindrical structure. As the weave of a double-woven artificial blood vessel, whose number of fiber layers is 2, a fabric such as a plain weave fabric, twill weave fabric, or a satin weave fabric, a variation thereof, or a multilayer fabric thereof may be used. As basic weaving methods, known means may be employed.

The artificial blood vessel is characterized in that it allows only a small amount of blood leakage and can achieve both the antithrombogenicity and the cellular affinity. Therefore, although our fabric is generally applicable to artificial blood vessels, it is especially suitable for artificial blood vessels having small inner diameters having poor long-term performances, and none of which is clinically useful. That is, the inner diameter is preferably 1 to 10 mm, more preferably 1 to 6 mm.

EXAMPLES

Our fabrics and artificial blood vessels are described below in detail by way of Examples and Comparative Examples. However, this disclosure is not limited thereto.

Example 1

As the warp yarns and the weft yarns constituting the inner-layer cylindrical fabric, polyethylene terephthalate multifilament yarns of 144 filaments having a single yarn fineness of 0.23 dtex and a total fineness of 33 dtex were used. As the warp yarns constituting the outer-layer cylindrical fabric, polyethylene terephthalate multifilament yarns of 24 filaments having a single yarn fineness of 2.33 dtex and a total fineness of 56 dtex were used. As the weft yarns constituting the outer-layer cylindrical fabric, polyethylene terephthalate monofilament yarns having a single yarn fineness of 33 dtex were used. The warp yarns were set in a narrow dobby double-shuttle loom, and the weft yarns were beaten up to perform weaving such that an inner diameter of 3 mm is achieved. Scouring was carried out at 98° C., and heat setting was carried out at 170° C., to obtain a multi-cylindrical fabric structure 1.

Thereafter, the cylindrical fabric 1 was immersed in an aqueous solution of 5.0 wt % potassium permanganate (manufactured by Wako Pure Chemical Industries, Ltd.) and 0.6 mol/L sulfuric acid (manufactured by Wako Pure Chemical Industries, Ltd.), and the reaction was allowed to proceed at 60° C. for 3 hours, thereby hydrolyzing and oxidizing the multi-cylindrical fabric structure 1.

Subsequently, the resulting product was immersed in an aqueous solution of 0.5 wt % DMT-MM (manufactured by Wako Pure Chemical Industries, Ltd.) and 5.0 wt % PEI (LUPASOL (registered trade mark) P, manufactured by BASF), and the reaction was allowed to proceed at 30° C. for 2 hours, thereby covalently binding PEI to the multi-cylindrical fabric structure 1 by condensation reaction.

Subsequently, the resulting product was immersed in 1 wt % aqueous methanol solution of ethyl bromide (manufactured by Wako Pure Chemical Industries, Ltd.), and the reaction was allowed to proceed at 35° C. for 1 hour, and then at 50° C. for 4 hours, thereby allowing modification of the PEI covalently bound to the surface of the multi-cylindrical fabric structure 1, with quaternary ammonium.

Finally, resulting product was immersed in an aqueous solution (pH 4) of 0.75 wt % heparin sodium (manufactured by Organon API Inc.) and 0.1 mol/L sodium chloride, and the reaction was allowed to proceed at 70° C. for 6 hours, thereby obtaining an artificial blood vessel (Sample 1) in which an antithrombogenic material layer is formed by ionic bonding with the PEI modified with quaternary ammonium.

The resulting artificial blood vessel (Sample 1) was subjected to evaluation of the blood leakage property, and evaluation of the antithrombogenicity and evaluation of the cellular affinity by artificial blood vessel transplantation tests for the dog carotid artery. The results are shown in Table 1. As shown in Table 1, in the evaluation of the blood leakage property, the amount of blood leakage was small so that the blood leakage property was evaluated as "Good". In the evaluation of the antithrombogenicity, no complete obstruction was found on Day 28 after the transplantation so that the antithrombogenicity was evaluated as "Good". In the evaluation of the cellular affinity, the distance of migration of vascular endothelial cells was long so that the cellular affinity was evaluated as "Good".

Example 2

The same operations as in Example 1 were carried out except that multifilament yarns having a single yarn fineness of 7.3 dtex and a total fineness 66 dtex, which are untwisted sea-island composite fibers (mixing ratio, sea/island (weight ratio)=20/80; island component number, 70), were used as the weft yarns constituting the inner-layer cylindrical fabric, and that, after the scouring, complete leaching of the sea component was carried out using 4 wt % aqueous sodium hydroxide (manufactured by Wako Pure Chemical Industries, Ltd.) solution at 98° C., followed by carrying out heat setting, to obtain polyethylene terephthalate multifilament yarns of 630 filaments having a single yarn fineness of 0.084 dtex and a total fineness 53 dtex. A multi-cylindrical fabric structure 2 was obtained by weaving.

In the sea-island composite fiber, the island component polymer is constituted by polyethylene terephthalate multifilament yarns, and the sea component polymer is constituted by polyethylene terephthalate copolymerized with 5-sodium sulfoisophthalate.

The resulting multi-cylindrical fabric structure 2 was subjected to the same operations as in Example 1 to obtain an artificial blood vessel in which an antithrombogenic material layer is formed (Sample 2).

The resulting artificial blood vessel (Sample 2) was subjected to evaluation of the blood leakage property, and evaluation of the antithrombogenicity and evaluation of the cellular affinity by artificial blood vessel transplantation tests for the dog carotid artery. The results are shown in Table 1. As shown in Table 1, in the evaluation of the blood leakage property, the amount of blood leakage was small so that the blood leakage property was evaluated as "Good". In the evaluation of the antithrombogenicity, no complete obstruction was found on Day 28 after the transplantation so that the antithrombogenicity was evaluated as "Good". In the evaluation of the cellular affinity, the distance of migration of vascular endothelial cells was long so that the cellular affinity was evaluated as "Good".

Example 3

The same operations as in Example 1 were carried out except that the multifilament yarns which are sea-island composite fibers used in Example 2 were used as the warp yarns and the weft yarns constituting the inner-layer cylindrical fabric, and that, after the scouring, complete leaching of the sea component was carried out using 4 wt % aqueous sodium hydroxide (manufactured by Wako Pure Chemical Industries, Ltd.) solution at 98° C., followed by carrying out heat setting, to obtain polyethylene terephthalate multifilament yarns of 630 filaments having a single yarn fineness of 0.084 dtex and a total fineness 53 dtex. A multi-cylindrical fabric structure 3 was obtained by weaving.

The resulting multi-cylindrical fabric structure 3 was subjected to the same operations as in Example 1 to obtain an artificial blood vessel in which an antithrombogenic material layer is formed (Sample 3).

The resulting artificial blood vessel (Sample 3) was subjected to evaluation of the blood leakage property, and evaluation of the antithrombogenicity and evaluation of the cellular affinity by artificial blood vessel transplantation tests for the dog carotid artery. The results are shown in Table 1. As shown in Table 1, in the evaluation of the blood leakage property, the amount of blood leakage was small so that the blood leakage property was evaluated as "Good". In the evaluation of the antithrombogenicity, no complete obstruction was found on Day 28 after the transplantation so that the antithrombogenicity was evaluated as "Good". In the evaluation of the cellular affinity, the distance of migration of vascular endothelial cells was long so that the cellular affinity was evaluated as "Good".

Example 4

By the same operations as in Example 1, the multi-cylindrical fabric structure 1 was hydrolyzed and oxidized, and PEI was covalently bound thereto by condensation reaction. The resulting product was then immersed in a solution of 0.5 wt % DMT-MM and 40 wt % succinic anhydride (manufactured by Wako Pure Chemical Industries, Ltd.) in dimethylacetamide, followed by allowing the reaction to proceed at 50° C. for 17 hours.

The resulting product was then immersed in an aqueous solution of 0.5 wt % DMT-MM and 5.0 wt % PEI, and the reaction was allowed to proceed at 30° C. for 2 hours. By the same operations as in Example 1, PEI was modified with quaternary ammonium using ethyl bromide, and heparin sodium was used to form an antithrombogenic material layer, thereby obtaining an artificial blood vessel (Sample 4).

The resulting artificial blood vessel (Sample 4) was subjected to evaluation of the blood leakage property, and evaluation of the antithrombogenicity and evaluation of the cellular affinity by artificial blood vessel transplantation tests for the dog carotid artery. The results are shown in Table 1. As shown in Table 1, in the evaluation of the blood leakage property, the amount of blood leakage was small so that the blood leakage property was evaluated as "Good". In the evaluation of the antithrombogenicity, no complete obstruction was found on Day 28 after the transplantation so that the antithrombogenicity was evaluated as "Good". In the evaluation of the cellular affinity, the distance of migration of vascular endothelial cells was long so that the cellular affinity was evaluated as "Good".

Example 5

By the same operations as in Example 1, the multi-cylindrical fabric structure 1 was hydrolyzed and oxidized, and PEI was covalently bound thereto by condensation reaction. The resulting product was then immersed in an aqueous solution of 0.5 wt % DMT-MM and 0.5 wt % PAA (weight average molecular weight, 1,000,000; manufactured by Wako Pure Chemical Industries, Ltd.), and the reaction was allowed to proceed at 30° C. for 2 hours.

The resulting product was then immersed in an aqueous solution of 0.5 wt % DMT-MM and 5.0 wt % PEI, and the reaction was allowed to proceed at 30° C. for 2 hours. By the same operations as in Example 1, PEI was modified with quaternary ammonium using ethyl bromide, and heparin sodium was used to form an antithrombogenic material layer, thereby obtaining an artificial blood vessel (Sample 5).

The resulting artificial blood vessel (Sample 5) was subjected to evaluation of the blood leakage property, and evaluation of the antithrombogenicity and evaluation of the cellular affinity by artificial blood vessel transplantation tests for the dog carotid artery. The results are shown in Table 1. As shown in Table 1, in the evaluation of the blood leakage property, the amount of blood leakage was small so that the blood leakage property was evaluated as "Good". In the evaluation of the antithrombogenicity, no complete obstruction was found on Day 28 after the transplantation so that the antithrombogenicity was evaluated as "Good". In the evaluation of the cellular affinity, the distance of migration of vascular endothelial cells was long so that the cellular affinity was evaluated as "Good".

Example 6

Artificial blood vessels were obtained by the same operations as in Example 5 except that polyallylamine hydrochloride (hereinafter referred to as "PAH") (weight average molecular weight, 900,000; manufactured by Sigma-Aldrich) or poly-L-lysine hydrobromide (hereinafter referred to as "PLys") (weight average molecular weight, 30,000 to 70,000; manufactured by Sigma-Aldrich) was used instead of PEI.

The artificial blood vessel in which an antithrombogenic material layer was formed using PAH was provided as Sample 6, and the artificial blood vessel in which an antithrombogenic material layer was formed using PLys was provided as Sample 7.

The resulting artificial blood vessels (Samples 6 and 7) were subjected to evaluation of the blood leakage property, and evaluation of the antithrombogenicity and evaluation of the cellular affinity by artificial blood vessel transplantation tests for the dog carotid artery. The results are shown in Table 1. As shown in Table 1, in the evaluation of the blood leakage property, the amount of blood leakage was small so that the blood leakage property was evaluated as "Good". In the evaluation of the antithrombogenicity, no complete obstruction was found on Day 28 after the transplantation so that the antithrombogenicity was evaluated as "Good". In the evaluation of the cellular affinity, the distance of migration of vascular endothelial cells was long so that the cellular affinity was evaluated as "Good".

Example 7

An artificial blood vessel in which an antithrombogenic material layer is formed (Sample 8) was obtained by the same operations as in Example 1 except that dextran sulfate sodium (manufactured by Wako Pure Chemical Industries, Ltd.) was used instead of heparin sodium.

The resulting artificial blood vessel (Sample 8) was subjected to evaluation of the blood leakage property, and evaluation of the antithrombogenicity and evaluation of the cellular affinity by artificial blood vessel transplantation tests for the dog carotid artery. The results are shown in Table 1. As shown in Table 1, in the evaluation of the blood leakage property, the amount of blood leakage was small so that the blood leakage property was evaluated as "Good". In the evaluation of the antithrombogenicity, no complete obstruction was found on Day 28 after the transplantation so that the antithrombogenicity was evaluated as "Good". In the evaluation of the cellular affinity, the distance of migration of vascular endothelial cells was long so that the cellular affinity was evaluated as "Good".

Example 8

By the same operations as in Example 1, the multi-cylindrical fabric structure 1 was hydrolyzed and oxidized. Thereafter, the resulting product was immersed in an aqueous solution in which 1.0 wt % Compound A (General Formula (X)), sodium hydroxide in an amount of 2 molar equivalents with respect to Compound A, and DMT-MM in an amount of 3 molar equivalents with respect to Compound A, are dissolved. The reaction was allowed to proceed at 30° C. for 2 hours to covalently bind Compound A to the cylindrical fabric 1 by condensation reaction, thereby obtaining an artificial blood vessel in which an antithrombogenic material layer is formed (Sample 9).

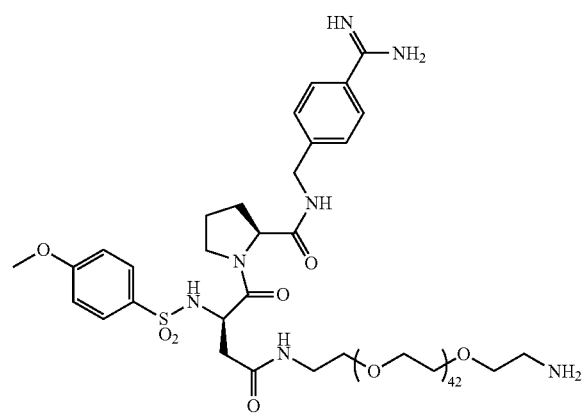

(X)

The resulting artificial blood vessel (Sample 9) was subjected to evaluation of the blood leakage property, and evaluation of the antithrombogenicity and evaluation of the cellular affinity by artificial blood vessel transplantation tests for the dog carotid artery. The results are shown in Table 1. As shown in Table 1, in the evaluation of the blood leakage property, the amount of blood leakage was small so that the blood leakage property was evaluated as "Good". In the evaluation of the antithrombogenicity, no complete obstruction was found on Day 28 after the transplantation so that the antithrombogenicity was evaluated as "Good". In the evaluation of the cellular affinity, the distance of migration of vascular endothelial cells was long so that the cellular affinity was evaluated as "Good".

Example 9

Artificial blood vessels were obtained by the same operations as in Example 8 except that Compound B (General Formula (XI)), Compound C (General Formula (XII)), or Compound D (General Formula (XIII)) was used instead of Compound A.

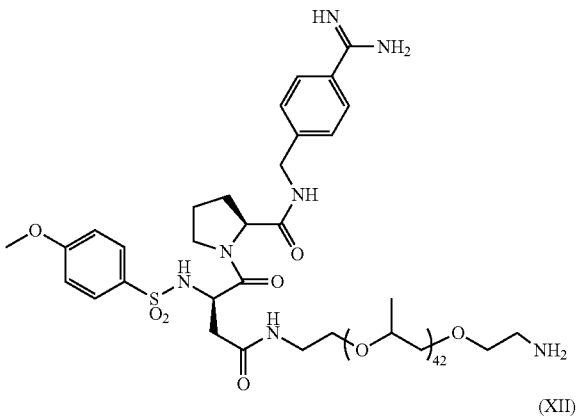

(XI)

(XII)

wherein n=42, and the degree of saponification (n'/n×100) is 85 to 90%

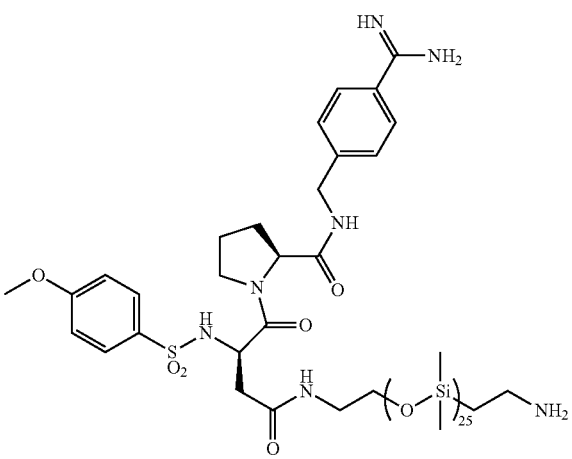

(XIII)

The artificial blood vessel in which an antithrombogenic material layer was formed using Compound B was provided as Sample 10; the artificial blood vessel in which an antithrombogenic material layer was formed using Compound C was provided as Sample 11; and the artificial blood vessel in which an antithrombogenic material layer was formed using Compound D was provided as Sample 12.

The resulting artificial blood vessels (Samples 10 to 12) were subjected to evaluation of the blood leakage property, and evaluation of the antithrombogenicity and evaluation of the cellular affinity by artificial blood vessel transplantation tests for the dog carotid artery. The results are shown in Table 1. As shown in Table 1, in the evaluation of the blood leakage property, the amount of blood leakage was small so that the blood leakage property was evaluated as "Good". In the evaluation of the antithrombogenicity, no complete obstruction was found on Day 28 after the transplantation so that the antithrombogenicity was evaluated as "Good". In the evaluation of the cellular affinity, the distance of migration of vascular endothelial cells was long so that the cellular affinity was evaluated as "Good".

Example 10

By the same operations as in Example 1, the multi-cylindrical fabric structure 1 was hydrolyzed and oxidized, and PEI was covalently bound thereto by condensation reaction. The resulting product was then immersed in an aqueous solution of 0.5 wt % DMT-MM and 0.5 wt % PAA (weight average molecular weight, 1,000,000; manufactured by Wako Pure Chemical Industries, Ltd.), and the reaction was allowed to proceed at 30° C. for 2 hours.

Thereafter, the resulting product was immersed in an aqueous solution in which 1.0 wt % Compound A, sodium hydroxide in an amount of 2 molar equivalents with respect to Compound A, and DMT-MM in an amount of 3 molar equivalents with respect to Compound A, are dissolved. The reaction was allowed to proceed at 30° C. for 2 hours to allow covalent bonding of Compound A by condensation reaction, thereby obtaining an artificial blood vessel in which an antithrombogenic material layer is formed (Sample 13).

The resulting artificial blood vessel (Sample 13) was subjected to evaluation of the blood leakage property, and evaluation of the antithrombogenicity and evaluation of the cellular affinity by artificial blood vessel transplantation tests for the dog carotid artery. The results are shown in Table 1. As shown in Table 1, in the evaluation of the blood leakage property, the amount of blood leakage was small so that the blood leakage property was evaluated as "Good". In the evaluation of the antithrombogenicity, no complete obstruction was found on Day 28 after the transplantation so that the antithrombogenicity was evaluated as "Good". In the evaluation of the cellular affinity, the distance of migration of vascular endothelial cells was long so that the cellular affinity was evaluated as "Good".

Example 11

Multi-cylindrical fabric structures were obtained by the same operations as in Example 1 except that polyethylene terephthalate monofilament yarns having a single yarn fineness of 13 dtex, polyethylene terephthalate monofilament yarns having a single yarn fineness of 108 dtex, or polyethylene terephthalate monofilament yarns having a single yarn fineness of 333 dtex were used as the weft yarns constituting the outer-layer cylindrical fabric.

The fabric woven using the polyethylene terephthalate monofilament yarns having a single yarn fineness of 13 dtex was provided as a multi-cylindrical fabric structure 4; the fabric woven using the polyethylene terephthalate monofilament yarns having a single yarn fineness of 108 dtex was provided as a multi-cylindrical fabric structure 5; and the fabric woven using the polyethylene terephthalate monofilament yarns having a single yarn fineness of 333 dtex was provided as a multi-cylindrical fabric structure 6.

The resulting multi-cylindrical fabric structures 4 to 6 were subjected to the same operations as in Example 1, to obtain artificial blood vessels in which an antithrombogenic material layer is foiined (Samples 14 to 16).

The resulting artificial blood vessels (Samples 14 to 16) were subjected to evaluation of the blood leakage property, and evaluation of the antithrombogenicity and evaluation of the cellular affinity by artificial blood vessel transplantation tests for the dog carotid artery. The results are shown in Table 1. As shown in Table 1, in the evaluation of the blood leakage property, the amount of blood leakage was small so that the blood leakage property was evaluated as "Good". In the evaluation of the antithrombogenicity, no complete obstruction was found on Day 28 after the transplantation so that the antithrombogenicity was evaluated as "Good". In the evaluation of the cellular affinity, the distance of migration of vascular endothelial cells was long so that the cellular affinity was evaluated as "Good".

Comparative Example 1

The same operations as in Example 1 were carried out except that polyethylene terephthalate multifilament yarns of 24 filaments having a single yarn fineness of 1.38 dtex and a total fineness of 33 dtex were used as the warp yarns constituting the inner-layer cylindrical fabric. A multi-cylindrical fabric structure 7 was obtained by weaving.

The resulting multi-cylindrical fabric structure 7 was subjected to the same operations as in Example 1, to obtain an artificial blood vessel in which an antithrombogenic material layer is formed (Sample 17), or subjected to the same operations as in Example 10, to obtain an artificial blood vessel in which an antithrombogenic material layer is formed (Sample 18).

The resulting artificial blood vessels (Samples 17 and 18) were subjected to evaluation of the blood leakage property, and evaluation of the antithrombogenicity and evaluation of the cellular affinity by artificial blood vessel transplantation tests for the dog carotid artery. The results are shown in Table 1. As shown in Table 1, in the evaluation of the blood leakage property, the amount of blood leakage was large so that the blood leakage property was evaluated as "Bad". Thus, the artificial blood vessels were not applicable to the artificial blood vessel transplantation tests for the dog carotid artery. That is, the antithrombogenicity and the cellular affinity were evaluated as "-".

Comparative Example 2

The same operations as in Example 1 were carried out except that polyethylene terephthalate multifilament yarns of 24 filaments having a single yarn fineness of 1.38 dtex and a total fineness of 33 dtex were used as the weft yarns constituting the inner-layer cylindrical fabric. A multi-cylindrical fabric structure 8 was obtained by weaving.

The resulting multi-cylindrical fabric structure 8 was subjected to the same operations as in Example 1, to obtain an artificial blood vessel in which an antithrombogenic material layer is formed (Sample 19), or subjected to the same operations as in Example 10, to obtain an artificial blood vessel in which an antithrombogenic material layer is formed (Sample 20).

The resulting artificial blood vessels (Samples 19 and 20) were subjected to evaluation of the blood leakage property, and evaluation of the antithrombogenicity and evaluation of the cellular affinity by artificial blood vessel transplantation tests for the dog carotid artery. The results are shown in Table 1. As shown in Table 1, in the evaluation of the blood leakage property, the amount of blood leakage was large so that the blood leakage property was evaluated as "Bad". Thus, the artificial blood vessels were not applicable to the artificial blood vessel transplantation tests for the dog carotid artery. That is, the antithrombogenicity and the cellular affinity were evaluated as "-".

Comparative Example 3

The same operations as in Example 1 were carried out except that weaving was carried out while the base fabric density was adjusted such that the cover factor was 1600, to obtain a multi-cylindrical fabric structure 9.

The resulting multi-cylindrical fabric structure 9 was subjected to the same operations as in Example 1, to obtain an artificial blood vessel in which an antithrombogenic material layer is formed (Sample 21), or subjected to the same operations as in Example 10, to obtain an artificial blood vessel in which an antithrombogenic material layer is formed (Sample 22).

The resulting artificial blood vessels (Samples 21 and 22) were subjected to evaluation of the blood leakage property, and evaluation of the antithrombogenicity and evaluation of the cellular affinity by artificial blood vessel transplantation tests for the dog carotid artery. The results are shown in Table 1. As shown in Table 1, in the evaluation of the blood leakage property, the amount of blood leakage was large so that the blood leakage property was evaluated as "Bad". Thus, the artificial blood vessels were not applicable to the artificial blood vessel transplantation tests for the dog carotid artery. That is, the antithrombogenicity and the cellular affinity were evaluated as "-".

Comparative Example 4

An artificial blood vessel (Sample 23) in which no antithrombogenic material layer is formed in the multi-cylindrical fabric structure 1 was obtained.

The resulting artificial blood vessel (Sample 23) was subjected to evaluation of the blood leakage property, and evaluation of the antithrombogenicity and evaluation of the cellular affinity by artificial blood vessel transplantation tests for the dog carotid artery. The results are shown in Table 1. As shown in Table 1, in the evaluation of the blood leakage property, the amount of blood leakage was small so that the blood leakage property was evaluated as "Good". However, in the evaluation of the antithrombogenicity, complete obstruction was found by Day 28 after the transplantation so that the antithrombogenicity was evaluated as "Bad". In the evaluation of the cellular affinity, no migration of vascular endothelial cells was found so that the cellular affinity was evaluated as "Bad".

Comparative Example 5

The multi-cylindrical fabric structure 1 was immersed in organic solvents such as methanol and tetrahydrofuran in which PEI, ethyl bromide, and heparin sodium are dissolved, to obtain an artificial blood vessel in which an antithrombogenic material layer is formed (Sample 24).

The resulting artificial blood vessel (Sample 24) was subjected to evaluation of the blood leakage property, and evaluation of the antithrombogenicity and evaluation of the cellular affinity by artificial blood vessel transplantation tests for the dog carotid artery. The results are shown in Table 1. As shown in Table 1, in the evaluation of the blood leakage property, the amount of blood leakage was small so that the blood leakage property was evaluated as "Good". In the evaluation of the antithrombogenicity, no complete obstruction was found on Day 28 after the transplantation so that the antithrombogenicity was evaluated as "Good". However, in the evaluation of the cellular affinity, the distance of migration of vascular endothelial cells was short so that the cellular affinity was evaluated as "Bad".

Example 12

The same operations as in Example 1 were carried out except that polyethylene terephthalate multifilament yarns of 144 filaments having a single yarn fineness of 0.30 dtex and a total fineness of 44 dtex were used as the warp yarns and the weft yarns constituting the inner-layer cylindrical fabric. A multi-cylindrical fabric structure 10 was obtained by weaving.

The resulting multi-cylindrical fabric structure 10 was subjected to the same operations as in Example 1, to obtain an artificial blood vessel in which an antithrombogenic material layer is formed (Sample 25).

The resulting artificial blood vessel (Sample 25) was subjected to evaluation of the blood leakage property, and evaluation of the antithrombogenicity and evaluation of the cellular affinity by artificial blood vessel transplantation tests for the dog carotid artery. The results are shown in Table 1. As shown in Table 1, in the evaluation of the blood leakage property, the amount of blood leakage was small so that the blood leakage property was evaluated as "Good". In the evaluation of the antithrombogenicity, no complete obstruction was found on Day 28 after the transplantation so that the antithrombogenicity was evaluated as "Good". In the evaluation of the cellular affinity, the distance of migration of vascular endothelial cells was long so that the cellular affinity was evaluated as "Good".

Example 13

The same operations as in Example 1 were carried out except that weaving was carried out while the base fabric density was adjusted such that the cover factor was 1700, to obtain a multi-cylindrical fabric structure 11.

The resulting multi-cylindrical fabric structure 11 was subjected to the same operations as in Example 1, to obtain an artificial blood vessel in which an antithrombogenic material layer is formed (Sample 26).

The resulting artificial blood vessel (Sample 26) was subjected to evaluation of the blood leakage property, and evaluation of the antithrombogenicity and evaluation of the cellular affinity by artificial blood vessel transplantation tests for the dog carotid artery. The results are shown in Table 1. As shown in Table 1, in the evaluation of the blood leakage property, the amount of blood leakage was small so that the blood leakage property was evaluated as "Good". In the evaluation of the antithrombogenicity, no complete obstruction was found on Day 28 after the transplantation so that the antithrombogenicity was evaluated as "Good". In the evaluation of the cellular affinity, the distance of migration of vascular endothelial cells was long so that the cellular affinity was evaluated as "Good".

The evaluation methods for the blood leakage property, antithrombogenicity, and cellular affinity of our artificial blood vessels are described below.

Evaluation 1: Blood Leakage Property

Similarly to the measurement of the water permeability described in the guidance in ISO 7198, a pressure (hydrostatic pressure) of 16 kPa was applied to the inner surface of an artificial blood vessel. Thirty seconds later, the amount of bovine blood (mL) flown out into the outer layer of the artificial blood vessel in 5 minutes was measured, and the amount was divided by the unit time (min.) and the unit area (cm$^2$), to determine the blood leakage property at 16 kPa. The bovine blood was prepared such that the hematocrit was 25 to 30%; the erythrocyte count was 5.0 to 6.2×10$^6$/μL; the leukocyte count was 30 to 110×10$^2$/μL; the platelet count was 6.0 to 20.0×10$^4$/μL; and the total protein was 6.5 g/dL. When the blood leakage property was less than 2.0 mL/cm$^2$/min, the amount of blood leakage was judged to be small, and the operation such as preclotting was thought to be unnecessary so that the blood leakage property was evaluated as "Good". When the blood leakage property was not less than 2.0 mL/cm$^2$/min., the amount of blood leakage was judged to be large, and the operation such as preclotting was thought to be necessary so that the blood leakage property was evaluated as "Bad".

Evaluation 2: Evaluation of Antithrombogenicity by Artificial Blood Vessel Transplantation Test for Dog Carotid Artery By referring to a document by P. C. Begovac et al. (Eur Vasc Endovasc Surg 25, 432-437 2003) and the like, an artificial blood vessel was transplanted to the dog carotid artery. The transplanted artificial blood vessel and the living blood vessels in both sides thereof were periodically subjected to ultrasound echo and angiography to judge the presence or absence of a thrombus/thrombi and the presence or absence of obstruction. On Day 28 after the transplantation, when no complete obstruction was found, the antithrombogenicity was judged to be high, and evaluated as "Good". When complete obstruction was found, the antithrombogenicity was judged to be insufficient, and evaluated as "Bad".

Evaluation 3: Evaluation of Cellular Affinity by Artificial Blood Vessel Transplantation Test for Dog Carotid Artery In the same manner as in Evaluation 2, an artificial blood vessel was transplanted to the dog carotid artery. The artificial blood vessel was removed on Day 28 after the transplantation, and stained with H. E. to prepare a sample. The sample obtained was observed under the microscope to measure the length from a suture site between the artificial blood vessel and a living blood vessel to the portion where vascular endothelial cells settled after migration. When the distance of migration of vascular endothelial cells was not less than 4.0 mm, the cellular affinity was judged to be high so that the cellular affinity was evaluated as "Good". When the distance of migration of vascular endothelial cells was less than 4.0 mm, the cellular affinity was judged to be insufficient so that the cellular affinity was evaluated as "Bad".

TABLE 1

| | | Inner layer | | Outer layer | | | | | | |
|---|---|---|---|---|---|---|---|---|---|---|
| | Sample | Warp yarn (dtex) | Weft yarn (dtex) | Warp yarn (dtex) | Weft yarn (dtex) | Water permeability (mL/cm$^2$/min.) | Cover factor | Antithrombogenic material | | |
| Example 1 | 1 | 0.23 | 0.23 | 2.33 | 33 | 34 | 2550 | Heparin | PEI | — |
| Example 2 | 2 | 0.23 | 0.084 | 2.33 | 33 | 130 | 2400 | Heparin | PEI | — |
| Example 3 | 3 | 0.084 | 0.084 | 2.33 | 33 | 208 | 2100 | Heparin | PEI | — |
| Example 4 | 4 | 0.23 | 0.23 | 2.33 | 33 | 21 | 2550 | Heparin | PEI | Succinic anhydride |
| Example 5 | 5 | 0.23 | 0.23 | 2.33 | 33 | 12 | 2550 | Heparin | PEI | PAA |
| Example 6 | 6 | 0.23 | 0.23 | 2.33 | 33 | 14 | 2550 | Heparin | PAH | PAA |
| | 7 | 0.23 | 0.23 | 2.33 | 33 | 14 | 2550 | Heparin | PLys | PAA |
| Example 7 | 8 | 0.23 | 0.23 | 2.33 | 33 | 34 | 2550 | Dextran sulfate | PEI | — |
| Example 8 | 9 | 0.23 | 0.23 | 2.33 | 33 | 27 | 2550 | Compound of General Formula (X) | — | — |
| Example 9 | 10 | 0.23 | 0.23 | 2.33 | 33 | 23 | 2550 | Compound of General Formula (XI) | — | — |
| | 11 | 0.23 | 0.23 | 2.33 | 33 | 32 | 2550 | Compound of General Formula (XII) | — | — |
| | 12 | 0.23 | 0.23 | 2.33 | 33 | 30 | 2550 | Compound of General Formula (XIII) | — | — |
| Example 10 | 13 | 0.23 | 0.23 | 2.33 | 33 | 17 | 2550 | Compound of General Formula (X) | PEI | PAA |
| Example 11 | 14 | 0.23 | 0.23 | 2.33 | 13 | 26 | 2550 | Heparin | PEI | — |
| | 15 | 0.23 | 0.23 | 2.33 | 108 | 62 | 2550 | Heparin | PEI | — |
| | 16 | 0.23 | 0.23 | 2.33 | 333 | 83 | 2550 | Heparin | PEI | — |
| Comparative Example 1 | 17 | 1.38 | 0.23 | 2.33 | 33 | 280 | 2100 | Heparin | PEI | — |
| | 18 | 1.38 | 0.23 | 2.33 | 33 | 275 | 2100 | Compound of General Formula (X) | PEI | PAA |
| Comparative Example 2 | 19 | 0.23 | 1.38 | 2.33 | 33 | 281 | 2150 | Heparin | PEI | — |
| | 20 | 0.23 | 1.38 | 2.33 | 33 | 273 | 2150 | Compound of General Formula (X) | PEI | PAA |
| Comparative Example 3 | 21 | 0.23 | 0.23 | 2.33 | 33 | 350 | 1600 | Heparin | PEI | — |
| | 22 | 0.23 | 0.23 | 2.33 | 33 | 320 | 1600 | Compound of General Formula (X) | PEI | PAA |
| Comparative Example 4 | 23 | 0.23 | 0.23 | 2.33 | 33 | 39 | 2550 | — | — | — |
| Comparative Example 5 | 24 | 0.23 | 0.23 | 2.33 | 33 | 10 | 2550 | Heparin | PEI | — |
| Example 12 | 25 | 0.30 | 0.30 | 2.33 | 33 | 57 | 2200 | Heparin | PEI | — |
| Example 13 | 26 | 0.23 | 0.23 | 2.33 | 33 | 251 | 1700 | Heparin | PEI | — |

| | Thickness (nm) | Abundance ratio of nitrogen atoms (atomic percent) | Abundance ratio of sulfur atoms (atomic percent) | Blood leakage property (mL/cm$^2$/min.) | Antithrombogenicity | Distance of migration (mm) |
|---|---|---|---|---|---|---|
| Example 1 | 58 | 8.2 | 3.8 | 0.04 | Good | 6.5 |
| Example 2 | 85 | 8.3 | 3.9 | 0.08 | Good | 9.8 |
| Example 3 | 85 | 8.3 | 3.8 | 1.8 | Good | 11 |

TABLE 1-continued

| | | | | | | |
|---|---|---|---|---|---|---|
| Example 4 | 510 | 8.0 | 3.3 | 0.10 | Good | 6.9 |
| Example 5 | 585 | 9.8 | 3.9 | 0.42 | Good | 5.3 |
| Example 6 | 483 | 9.1 | 3.2 | 0.51 | Good | 5.1 |
| | 495 | 9.2 | 3.0 | 0.48 | Good | 5.1 |
| Example 7 | 60 | 8.2 | 3.6 | 0.08 | Good | 4.9 |
| Example 8 | 45 | — | — | 0.32 | Good | 4.9 |
| Example 9 | 42 | — | — | 0.40 | Good | 4.9 |
| | 43 | — | — | 0.40 | Good | 4.3 |
| | 42 | — | — | 0.41 | Good | 4.5 |
| Example 10 | 470 | — | — | 0.42 | Good | 5.2 |
| Example 11 | 58 | 8.2 | 4.0 | 0.04 | Good | 6.4 |
| | 60 | 8.1 | 3.6 | 0.10 | Good | 6.3 |
| | 57 | 8.4 | 3.8 | 0.11 | Good | 6.5 |
| Comparative Example 1 | 35 | 8.2 | 4.1 | 4.5 | — | — |
| | 470 | — | — | 4.2 | — | — |
| Comparative Example 2 | 38 | 8.2 | 3.8 | 4.2 | — | — |
| | 470 | — | — | 4.3 | — | — |
| Comparative Example 3 | 60 | 8.0 | 3.5 | 16 | — | — |
| | 470 | — | — | 18 | — | — |
| Comparative Example 4 | 0 | — | — | 0.01 | Bad | 0 |
| Comparative Example 5 | 650 | 12.8 | 6.3 | 0.01 | Good | 1.2 |
| Example 12 | 58 | 8.2 | 3.8 | 0.44 | Good | 4.1 |
| Example 13 | 58 | 8.2 | 3.8 | 1.9 | Good | 4.5 |

INDUSTRIAL APPLICABILITY

Our artificial blood vessel can be favorably used in the field of medicine as a fabric artificial blood vessel which allows only a small amount of blood leakage and can achieve both the antithrombogenicity and the cellular affinity.

The invention claimed is:

1. An artificial blood vessel comprising a substantially cylindrical fabric structure having at least a cylindrical fabric whose inside contacts blood,
wherein
said cylindrical fabric whose inside contacts blood is a fabric prepared by interlacing a plurality of warp yarns and a plurality of weft yarns with each other into a cylindrical shape;
said warp yarns and said weft yarns constituting said cylindrical fabric whose inside contacts blood comprise a multifilament yarn having a single yarn fineness of not more than 0.50 dtex, and are bound to an antithrombogenic material;
said antithrombogenic material forms an antithrombogenic material layer having a thickness of 1 to 600 nm inside said cylindrical fabric whose inside contacts blood;
water permeability under conditions where a pressure of 16 kPa is applied to an inner surface of said cylindrical fabric whose inside contacts blood is less than 300 mL/cm²/min;
said substantially cylindrical fabric structure is a multi-cylindrical fabric structure further comprising an outer-layer cylindrical fabric arranged outside said cylindrical fabric whose inside contacts blood, and said outer-layer cylindrical fabric is a fabric formed by interlacing a plurality of warp yarns and a plurality of weft yarns with each other into a cylindrical shape; and
said outer-layer cylindrical fabric comprises, as a warp yarn, a multifilament yarn having a single yarn fineness of not less than 1.0 dtex.

2. The artificial blood vessel according to claim 1, wherein a percentage of exposure of said multifilament yarn having a single yarn fineness of not less than 1.0 dtex on said inner surface is not more than 20%.

3. The artificial blood vessel according to claim 1, wherein the cover factor for said warp yarns and said weft yarns constituting said substantially cylindrical fabric whose inside contacts blood is 1800 to 4000.

4. The artificial blood vessel according to claim 1, wherein said outer-layer cylindrical fabric comprises, as a weft yarn, a monofilament yarn having a single yarn fineness of not less than 15.0 dtex.

5. The artificial blood vessel according to claim 1, wherein said antithrombogenic material comprises a cationic polymer containing, as a constituent monomer, a compound selected from the group consisting of alkyleneimines, vinylamines, allylamines, lysine, protamine, and diallyldimethylammonium chloride, and said cationic polymer is covalently bound to said warp yarns and said weft yarns constituting said cylindrical fabric whose inside contacts blood.

6. The artificial blood vessel according to claim 5, wherein said antithrombogenic material further comprises: an anionic polymer comprising, as a constituent monomer, a compound selected from the group consisting of acrylic acid, methacrylic acid, α-glutamic acid, γ-glutamic acid, and aspartic acid; or an anionic compound selected from the group consisting of oxalic acid, malonic acid, succinic acid, fumaric acid, glutaric acid, adipic acid, pimelic acid, suberic acid, azelaic acid, sebacic acid, malic acid, tartaric acid, and citric acid.

7. The artificial blood vessel according to claim 1, wherein said multifilament yarn is composed of a polyester.

* * * * *